(12) United States Patent
Ellingson et al.

(10) Patent No.: US 9,993,232 B2
(45) Date of Patent: Jun. 12, 2018

(54) BIOPSY WITH MARKER DEVICE AND METHOD

(71) Applicants: Andrew N. Ellingson, Bettendorf, IA (US); David I. Ellingson, Webster City, IA (US)

(72) Inventors: Andrew N. Ellingson, Bettendorf, IA (US); David I. Ellingson, Webster City, IA (US)

( * ) Notice: Subject to any disclaimer, the term of this patent is extended or adjusted under 35 U.S.C. 154(b) by 259 days.

(21) Appl. No.: 14/710,846

(22) Filed: May 13, 2015

(65) Prior Publication Data
US 2015/0335317 A1 Nov. 26, 2015

Related U.S. Application Data

(60) Provisional application No. 62/001,783, filed on May 22, 2014.

(51) Int. Cl.
*A61B 10/00* (2006.01)
*A61B 10/02* (2006.01)
*A61B 90/00* (2016.01)

(52) U.S. Cl.
CPC ...... *A61B 10/0266* (2013.01); *A61B 10/0275* (2013.01); *A61B 2010/0208* (2013.01); *A61B 2090/3904* (2016.02); *A61B 2090/3908* (2016.02); *A61B 2090/3987* (2016.02)

(58) Field of Classification Search
CPC ............ A61B 10/0266; A61B 10/0275; A61B 2010/0208; A61B 2090/3904; A61B 2090/3908; A61B 2090/3987
See application file for complete search history.

(56) References Cited

U.S. PATENT DOCUMENTS

| | | | |
|---|---|---|---|
| 4,840,184 A | 6/1989 | Garg | |
| 4,844,087 A | 7/1989 | Garg | |
| 5,782,775 A | 7/1998 | Milliman et al. | |
| 6,056,700 A | 5/2000 | Burney et al. | |
| 6,220,248 B1 | 4/2001 | Voegele et al. | |
| 6,261,243 B1 | 7/2001 | Burney et al. | |
| 6,261,302 B1 | 7/2001 | Voegele et al. | |
| 6,432,064 B1 | 8/2002 | Hibner et al. | |
| 6,766,186 B1 | 7/2004 | Hoyns et al. | |
| 7,169,114 B2 | 1/2007 | Krause | |
| 7,465,279 B2 | 12/2008 | Beckman et al. | |
| 7,693,567 B2 | 4/2010 | Tsonton et al. | |
| 7,819,820 B2 | 10/2010 | Field et al. | |
| 7,862,517 B2 | 1/2011 | Tsonton et al. | |
| 7,895,725 B2 * | 3/2011 | Beckman | A61B 10/0275 29/458 |
| 8,050,741 B2 | 11/2011 | Ashby et al. | |
| 8,062,230 B1 | 11/2011 | Mark et al. | |
| 8,105,243 B2 | 1/2012 | Vetter | |
| 8,167,817 B2 | 5/2012 | Vetter et al. | |
| 8,262,585 B2 | 9/2012 | Thompson et al. | |
| 8,267,868 B2 | 9/2012 | Taylor et al. | |

(Continued)

*Primary Examiner* — Devin Henson

(57) ABSTRACT

A biopsy device to remove tissue from a patient and place a marker in the patient. The device includes a needle with an opening where tissue enters. The tissue which enters the opening is cut and stored in the device. After the desired number of tissue samples are obtained, a marker is released from the same needle opening. The biopsy sampling and marker release are integrated for one hand operation in a single device.

18 Claims, 33 Drawing Sheets

(56) References Cited

U.S. PATENT DOCUMENTS

| | | | |
|---|---|---|---|
| 8,282,574 B2 | 10/2012 | Coonahan et al. | |
| 8,529,465 B2 | 9/2013 | Speeg et al. | |
| 8,721,563 B2 | 5/2014 | Tayor et al. | |
| 8,728,003 B2 | 5/2014 | Taylor et al. | |
| 8,771,200 B2 | 7/2014 | Thompson et al. | |
| 8,864,682 B2 | 10/2014 | Hibner | |
| 8,938,285 B2 | 1/2015 | Fiebig et al. | |
| 2003/0050571 A1* | 3/2003 | Zarins | A61B 10/0275 600/562 |
| 2006/0217635 A1 | 9/2006 | McCombs et al. | |
| 2008/0188768 A1 | 8/2008 | Zarins et al. | |
| 2011/0144533 A1* | 6/2011 | Chudzik | A61B 10/0275 600/567 |
| 2012/0065542 A1 | 3/2012 | Hibner et al. | |
| 2012/0330186 A1 | 12/2012 | Rhad et al. | |
| 2013/0237912 A1 | 9/2013 | Speeg | |
| 2014/0039343 A1 | 2/2014 | Mescher et al. | |
| 2014/0051996 A1 | 2/2014 | Sirimanne et al. | |
| 2014/0081170 A1 | 3/2014 | Parihar et al. | |
| 2014/0088412 A1 | 3/2014 | Ritchart et al. | |
| 2014/0094713 A1 | 4/2014 | Hibner | |
| 2014/0094714 A1 | 4/2014 | Leimbach et al. | |
| 2014/0100478 A1 | 4/2014 | Speeg et al. | |
| 2014/0107528 A1 | 4/2014 | Beckman et al. | |
| 2014/0135649 A1 | 5/2014 | Moore et al. | |
| 2014/0275999 A1 | 9/2014 | Speeg et al. | |
| 2014/0276037 A1 | 9/2014 | Johnson et al. | |
| 2014/0276209 A1 | 9/2014 | Hibner et al. | |
| 2014/0336531 A1 | 11/2014 | Fiebig et al. | |

\* cited by examiner

BIOPSY WITH MARKER DEVICE AND METHOD

CROSS-REFERENCE TO RELATED APPLICATIONS

This application claims priority to U.S. Provisional Patent Application Ser. No. 62/001,783 filed May 22, 2014, titled "Biopsy With Marker Device and Method", the entire contents of which is incorporated herein, both bodily and by reference.

FEDERALLY SPONSORED RESEARCH

Not Applicable

SEQUENCE LISTING OR PROGRAM

Not Applicable

FIELD OF THE INVENTION

The present invention relates to deploying a clip marker for implantation in tissue of a surgical patient and more particularly, to incorporate the deployment mechanism with a tissue biopsy device.

BACKGROUND OF THE INVENTION

Biopsy samples have been obtained in a variety of ways with various medical devices. An example biopsy device is disclosed in U.S. Pat. No. 8,864,682, entitled "Clutch and Valving System for Tetherless Biopsy Device", issued Oct. 21, 2014.

Biopsy marker clips have been deployed in a variety of ways with various medical devices. An example marker clip deployment device is disclosed in U.S. Pub. No. 2013/0237912, entitled "Biopsy Marker Delivery Device", published Sep. 12, 2013. Another example marker clip deployment device is disclosed in U.S. Pat. No. 6,261,302, entitled "Applier for Implantable Surgical Marker", issued Jul. 17, 2001.

A typical biopsy procedure is to use a tetherless device such as described in U.S. Pat. No. 8,864,682. A cannula tube would be installed over the device needle. The cannula tube/device needle would be inserted into the patient and the tissue sample obtained. The cannula would be left in place when the device needle is removed. Keeping the cannula from moving during device needle removal or after is an important procedure task.

A typical marker delivery procedure would then follow using a device such as described in US2013/0237912. The goal of the clip marker deployment is to place the clip marker as accurately as possible to the site where the tissue sample was removed. The deployment device would be inserted into the patient though the cannula. Again, keeping the cannula from moving during delivery device insertion is an important procedure task. The amount of insertion depth is another important procedure task.

The biopsy device (which has been removed from the cannula) obtained the tissue sample from the needle window at a specific angular orientation relative to the axis of the cannula. For accurate clip marker placement, it is important for the deployment device window be along the same angular orientation as the biopsy needle window during the moment of tissue sample. Rotating the deployment device within the cannula to align with the biopsy device needle window is another important procedure task.

The clip marker is then deployed with a manual pushing of a knob on the marker delivery device.

If the lesion is small, or has been completely removed during the biopsy procedure, it is critical to keep the ultrasound probe localized to the area of the procedure during the marker clip placement. This often requires two people, as one hand is required to hold the ultrasound transducer so as to not lose the procedure site, a second hand is required to hold the cannula, and a third hand is required to remove the device needle. A device that allows this step to be performed by one person would be advantageous.

Integration of the biopsy device with marker clip deployment has been disclosed in a variety of ways with various medical devices. An example integrated deployment device is disclosed in U.S. Pat. No. 8,728,003, entitled "Single Insertion, Multiple Sample Biopsy Device With Integrated Markers", issued May 20, 2014. Another example integrated deployment device is disclosed in U.S. Pat. No. 8,167,817, entitled "Methods And Devices For Removing Tissue From A Patient And Placing A Marker In The Patient", issued May 1, 2012.

A limitation of these integrated deployment devices is that the marker clip does not include a pledget. The pledget surrounds the marker clip and facilitates the implatation of the marker clip to the surrounding tissue. Another limitation is the use of a low force deployment method such as springs. A high force method ensures reliable marker clip deployment. Another limitation is re-direction of the marker clip motion such as side loading into the needle axis. Keeping the motion of the marker clip in a straight line until exit from the needle window ensures reliable deployment.

The disclosure of each of the above-cited U.S. Patents, U.S. patent application Publications, U.S. Provisional Patent Applications, and U.S. Non-Provisional patent application is incorporated by reference herein.

SUMMARY OF THE INVENTION

The present invention combines the functions of the biopsy device and the marker delivery device into one mechanism. It removes the tissue sample from a needle side opening window and then deploys the clip marker from this sample needle side opening window. The tissue sample is removed and the clip marker deployed with one needle insertion, thus the need for the cannula tube is eliminated.

The cannula tube increases the total insertion needle diameter. Eliminating this tube allows a smaller needle diameter and will reduce patient tissue damage.

The present invention will save time for the doctor doing the procedure. All of the procedure steps up to the tissue sample being obtained are approximately the same. After the tissue sample, the doctor will then withdraw the biopsy needle approximately 10 mm. This is to align the clip marker exit point to the center of the biopsy needle aperture where the tissue sample was obtained. The doctor will then press one button on the biopsy device to automatically deploy the clip marker.

The time savings will include all the steps of inserting, aligning and manually pushing the clip marker deployment with the marker delivery device. This time savings will also be of benefit to the patient having the procedure.

The present invention eliminates the procedure task of keeping the cannula task position. It eliminates the procedure task of angular alignment between biopsy device and marker delivery device. It reduces the depth procedure task to one set dimension withdrawal of the biopsy device (10 mm.)

The present invention provides more accurate clip marker placement. The elimination of several procedure steps and the immediacy of the clip delivery will allow the clip marker to be placed very close to the tissue sample removal location and allows the procedure to be performed by a single operator, without the need for an assistant to hold the ultrasound probe.

The present invention will save material cost. Along with the cannula, no separate clip marker delivery device is needed.

The clip marker deployment mechanism fully integrates with the biopsy device. Only small changes in size, weight and operation of the device are required.

Figure 1:
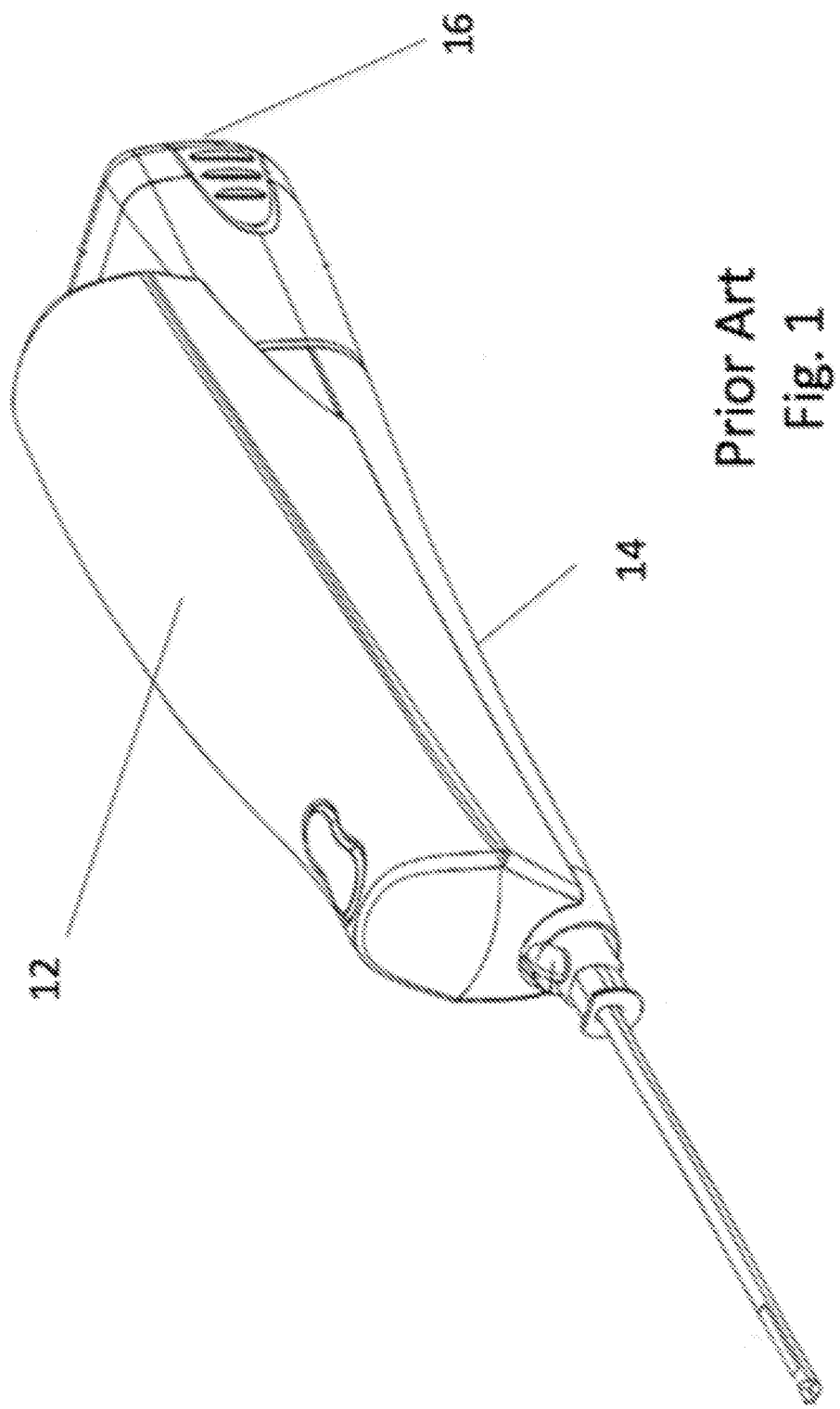
FIG. 1 is an isometric view of a prior art biopsy device.

| REFERENCE NUMERALS | | | |
|---|---|---|---|
| 12 | handle assembly | 14 | needle assembly |
| 16 | basket assembly | 22 | needle tip |
| 24 | cutter tube | 26 | needle tube |
| 32 | vacuum tube | 46 | vacuum pump |
| 48 | vacuum port | 55 | basket case |
| 57 | basket release | 72 | tissue sample |
| 91 | needle assembly | 93 | handle assembly |
| 95 | needle tip | 97 | basket cover |
| 100 | cutter tube | 101 | saline tank |
| 102 | saline tank cap | 103 | saline pump |
| 104 | vacuum port | 105 | saline tube |
| 106 | marker tube | 107 | basket |
| 108 | basket case | 110 | marker assembly |
| 111 | drive rod | 112 | drive plug |
| 113 | tube support | 114 | tube support |
| 120 | basket seal | 122 | tube seal |
| 123 | tube seal | 124 | basket cover weld |
| 126 | tube weld | 128 | lead in ramp |
| 129 | lead in ramp | 130 | flap |
| 132 | flap bar | 140 | tissue sample |
| 170 | aperture | 172 | end of cutter tube |
| 180 | needle tube | 182 | ramp |
| 184 | vacuum tube | 186 | cutter tube pocket |
| 192 | vacuum lumen | 200 | marker clip |
| 201 | pledget | 262 | rod tip |
| 280 | marker sense tube | 281 | marker bellows |
| 282 | marker switch plunger | 283 | marker switch |
| 284 | rod sense tube | 285 | rod bellows |
| 286 | rod switch plunger | 287 | rod switch |
| 292 | cover rod | 294 | push rod |
| 296 | drive wheel | 298 | push tube |
| 312 | drive wheel axle | 314 | opening |
| 330 | handle | 332 | manual rod |
| 334 | manual tube | 335 | lead in ramp |

DETAILED DESCRIPTION OF THE DRAWINGS

FIG. 1 is an isometric view of a prior art biopsy device. The biopsy device is composed of three main assemblies. These include the needle assembly 14, the handle assembly 12 and the basket assembly 16. All of the patient contact, tissue and any fluids is contained within or on the needle assembly 14 or basket assembly 16. These assemblies are packaged sterile one time use assemblies. The handle assembly 12 is designed for reuse and has no contact with patient, tissue or fluids. As much as possible, components are included in the handle where possible. Typically, the handle assembly 12 includes the microprocessor control, display, control switch(es), battery, motor(s), gears and shafts.

Figure 2:
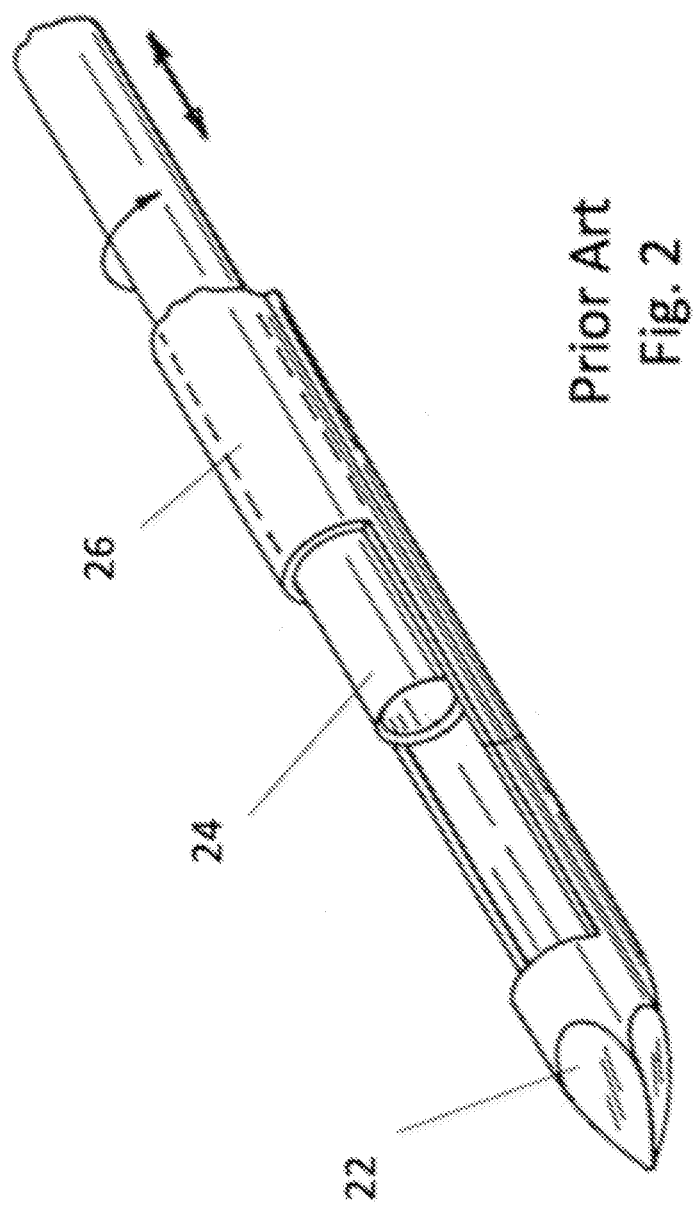
FIG. 2 is an isometric view of a prior art biopsy needle.

FIG. 2 is an isometric view of a prior art biopsy needle. The biopsy needle is part of the needle assembly 14. The needle tip 22 is fixed to the end of the needle tube 26. The cutter tube 24 rotates and move longitudinally inside the needle tube 26.

Figure 3:
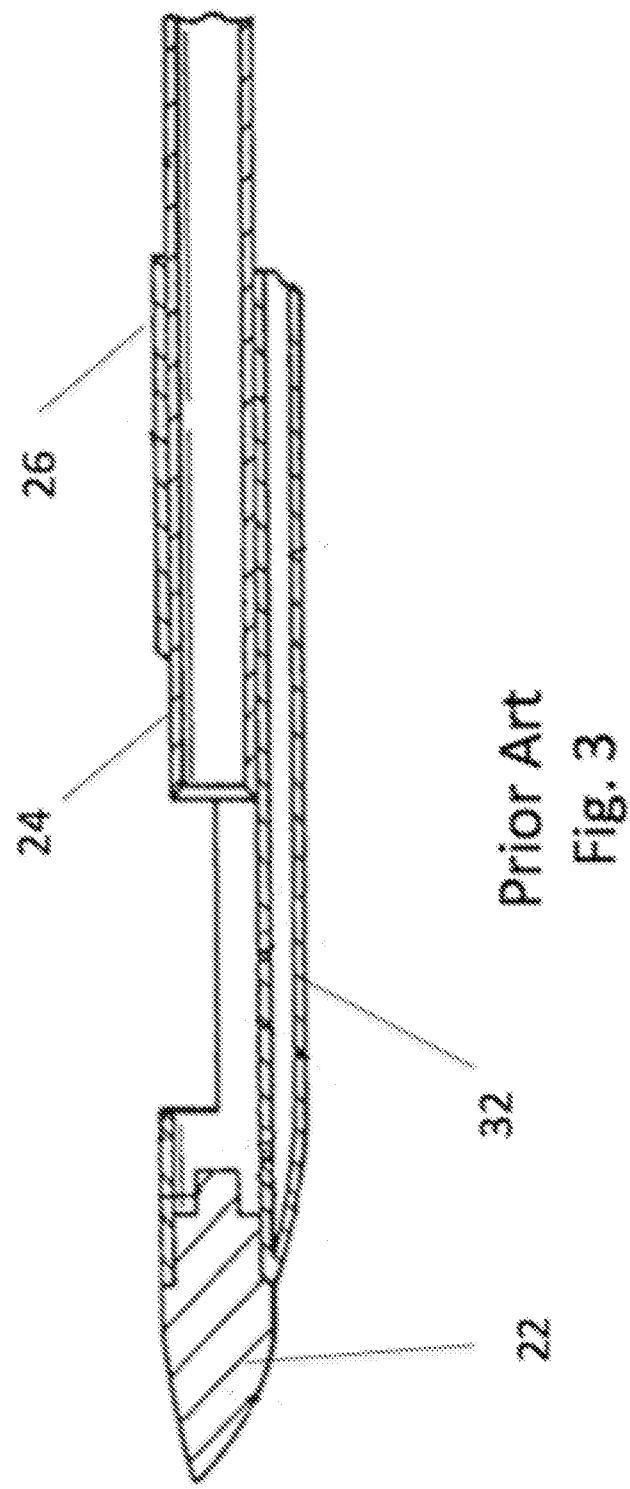
FIG. 3 is a side view in cross section of a prior art needle tip.

FIG. 3 is a side view in cross section of a prior art needle tip. The biopsy needle is composed of the needle tip 22, needle tube 24, cutter tube 26 and vacuum tube 32.

Figure 4:
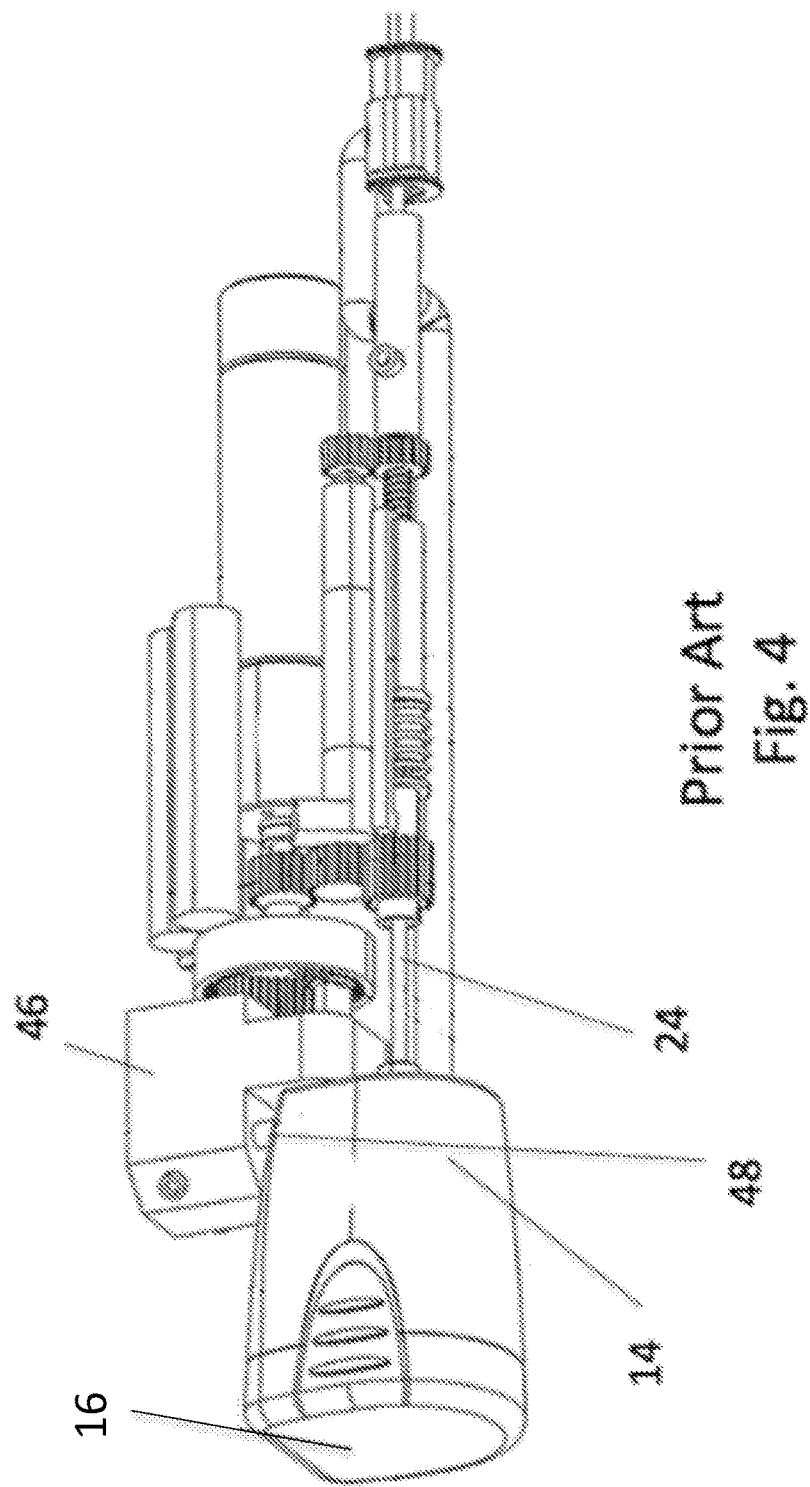
FIG. 4 is an isometric view of the internal parts of a prior art biopsy device.

FIG. 4 is an isometric view of the internal parts of a prior art biopsy device. The needle tube 26 terminates after the drive train gears. This leaves the cutter tube 24 exposed prior to the basket case 55. The vacuum port 48 provides a conduit between the vacuum pump 46 and the basket case 55.

Figure 5:
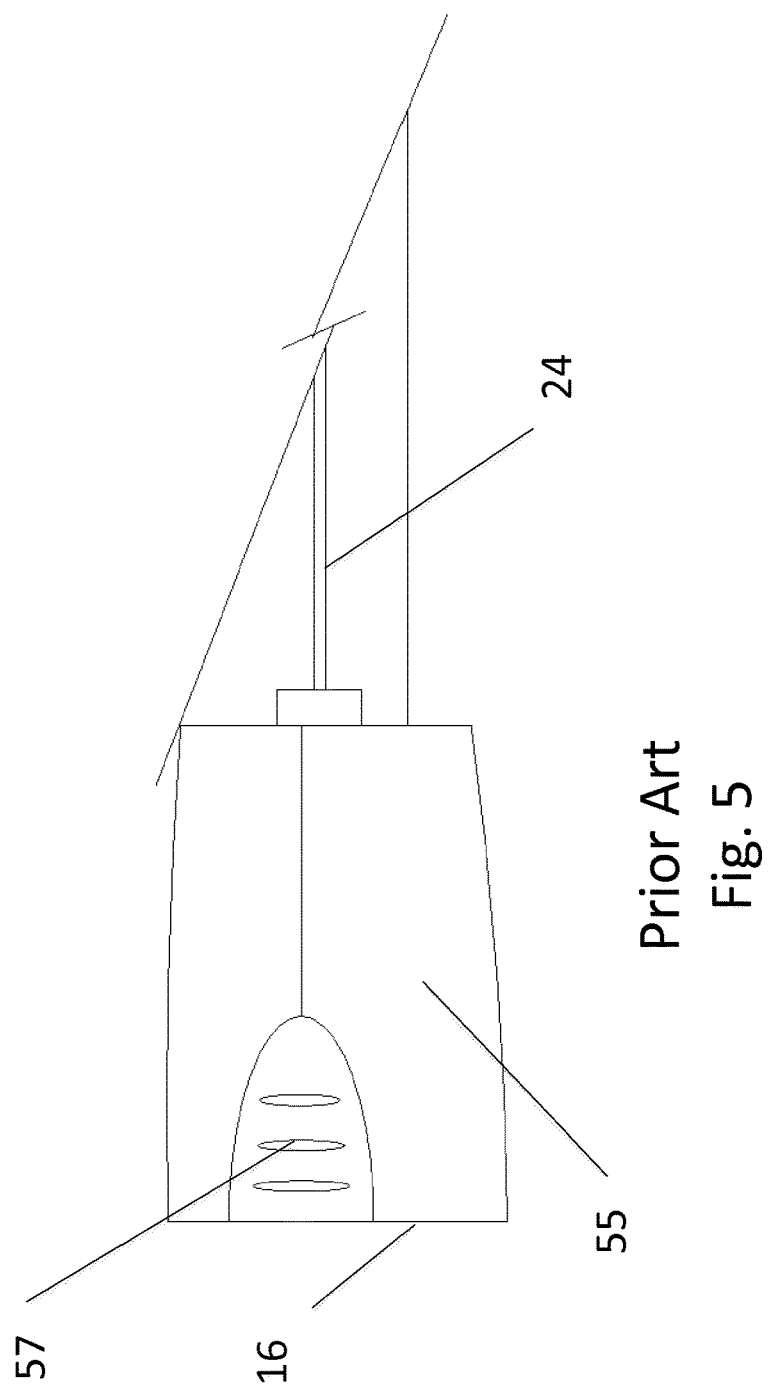
FIG. 5 is a side view of a prior art biopsy device.

FIG. 5 is a side view of a prior art biopsy device. The basket 16 is removeable from the basket case 55 by squeezing the basket release 57 and pulling out.

Figure 6:
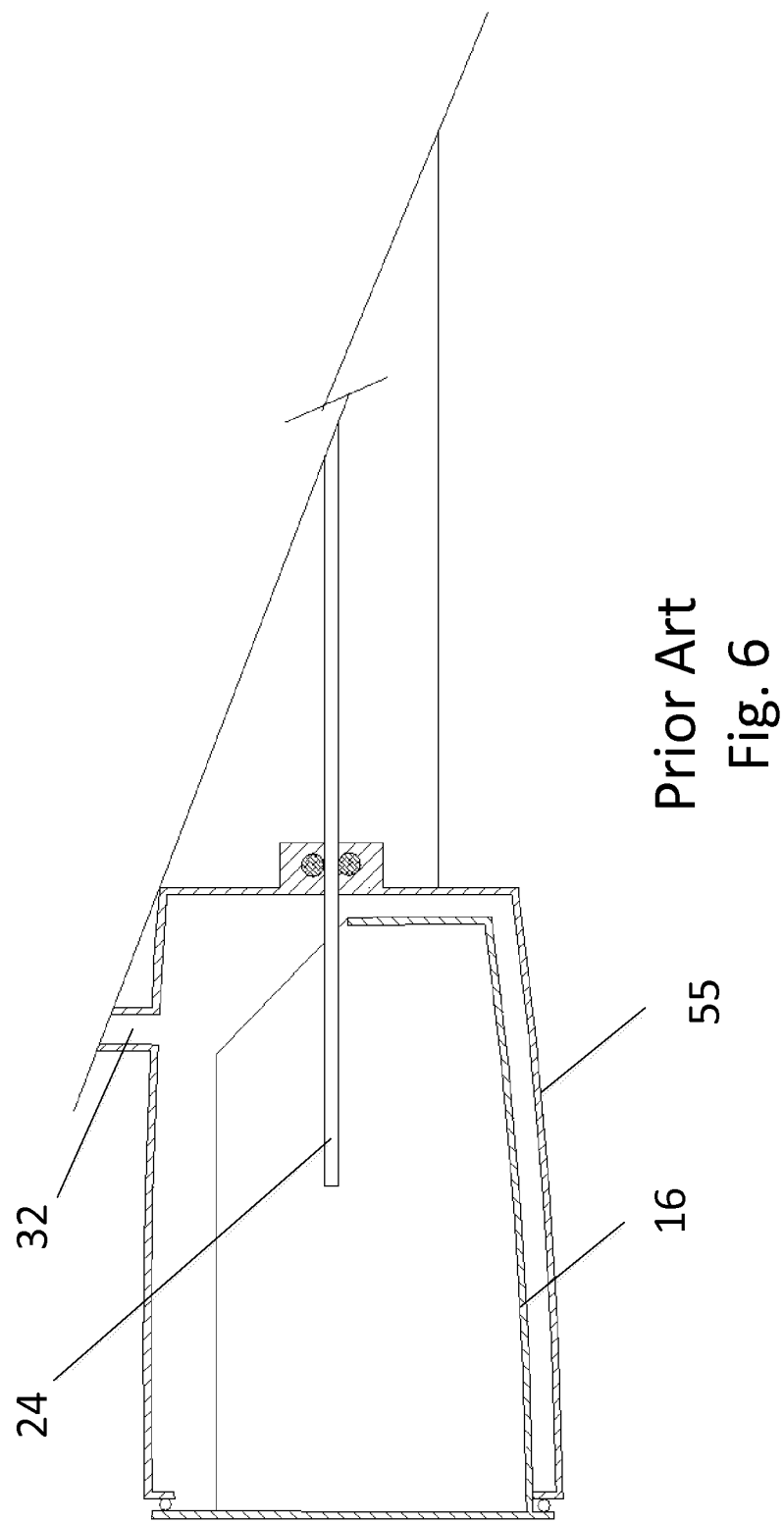
FIG. 6 is a side view in cross section of a prior art biopsy device.

FIG. 6 is a side view in cross section of a prior art biopsy device. The cutter tube 24 extends into the basket 16. The vacuum port 32 connects to the basket case 55. The cutter tube 24 in FIG. 6 is shown in the retracted position (needle aperture open).

Figure 7:
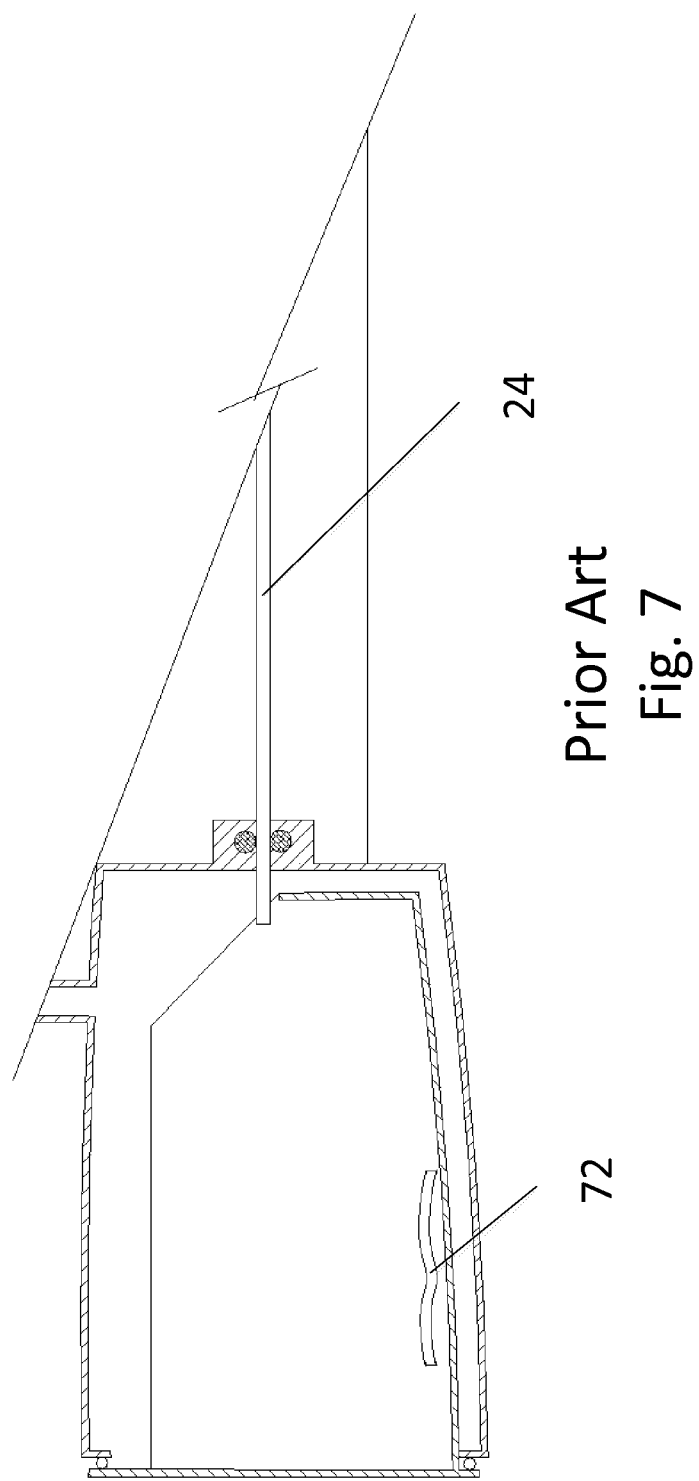
FIG. 7 is a side view in cross section of a prior art biopsy device after sample collection.

FIG. 7 is a side view in cross section of a prior art biopsy device after sample collection. The cutter tube 24 is now shown in the forward position (needle aperture closed). After this forward motion of the cutter tube 24, the tissue sample 72 would be pulled through the cutter tube 24 due to a vacuum within the basket case 55.

Figure 8:
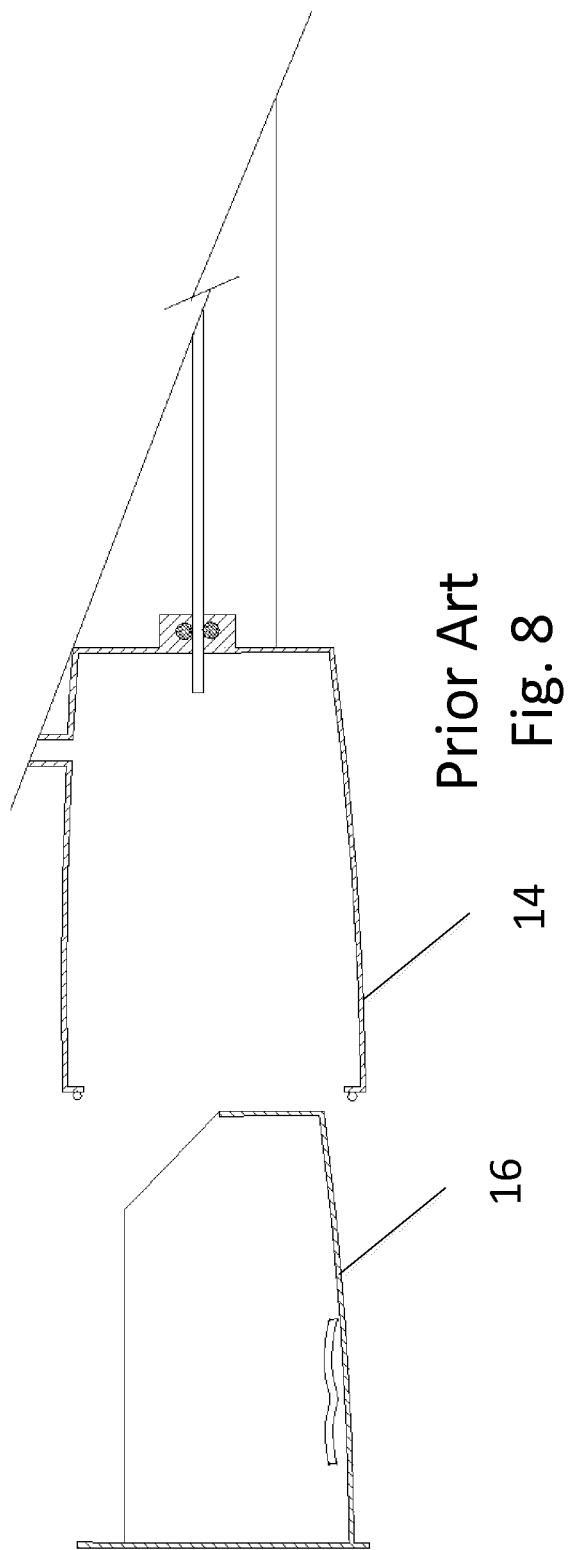
FIG. 8 is a side view in cross section of a prior art biopsy device with sample basket removed.

FIG. 8 is a side view in cross section of a prior art biopsy device with basket assembly 16 removed.

Figure 9:
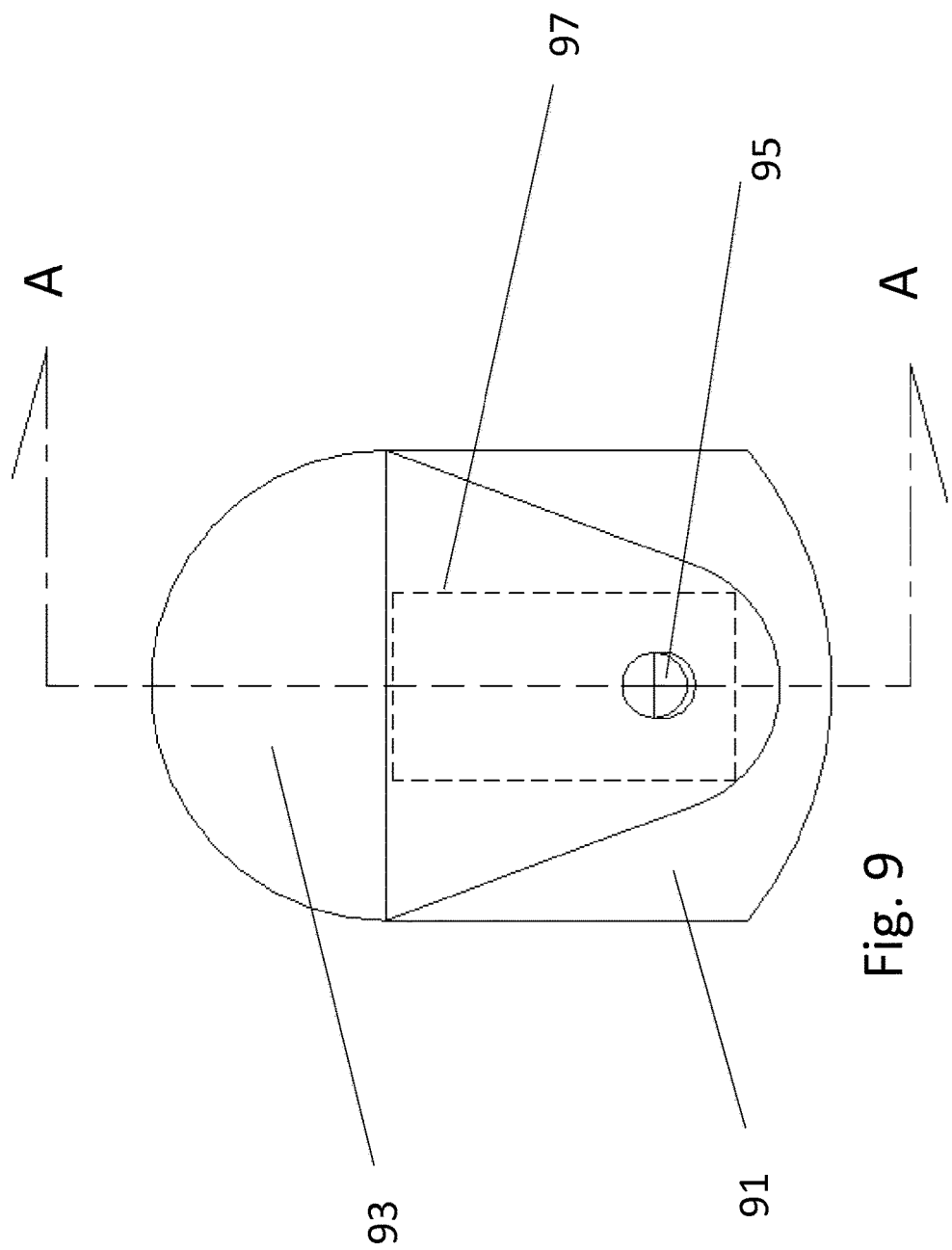
FIG. 9 is a front view of the needle end of the device.

FIG. 9 is a front view of the needle end of the device. The present invention includes a handle assembly 93 which is reusable. The needle assembly 91 is intended for one time use. The needle tip 95 is used for reference on several section view to follow. The basket cover 97 is shown with hidden lines. It is positioned at the rear of the device.

Figure 10:
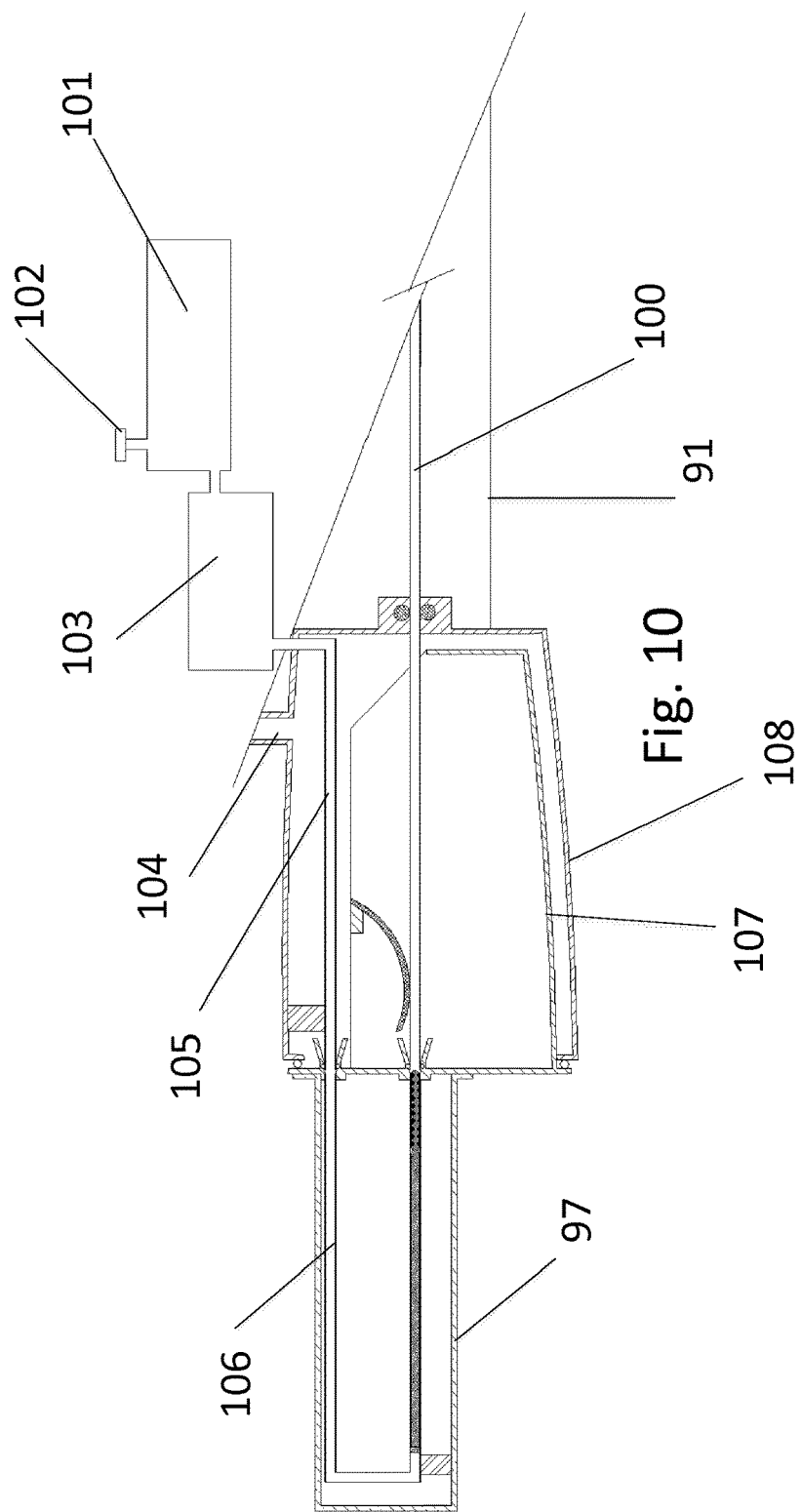
FIG. 10 is a section view of the handle end, device ready for use, taken along section line A-A from FIG. 9.

FIG. 10 is a section view of the handle end, device ready for use, taken along section line A-A from FIG. 9. Shown in schematic format are the saline tank 101, saline tank cap 102 and saline pump 103. Those skilled in the art would understand how to incorporate these components into the structure of the device.

The saline tank 101 and saline tank cap 102 would be located in the disposable needle assembly 91. The saline pump 103 would be split with the housing and impeller in the needle assembly 91. The motor for the saline pump 103 would be located in the handle assembly 93.

The saline tank 101 would be manually filled with sterile saline prior to the procedure. Other sterile fluids such a water would also function in the device. In an alternate construction, it may be possible to automatically fill the saline tank 100 with the output of the vacuum pump. The vacuum pump and other mechanism of the prior art are not detailed on this figure. U.S. Pat. No. 8,864,682 is a reference for the various components needed to cause the cutter tube motion, vacuum function, batteries and user controls.

In another alternate construction, it may be possible to use a pneumatic rather than a hydraulic system. The pnuematic approach would utilize an air compressor and would not require a fluid tank.

The basket case 108 is part of the needle assembly 91. The vacuum port 104 operates similar to the prior art and interacts with the basket case 108. The cutter tube 100 is shown in the retracted position. The basket cover 97 houses the marker tube 106. The saline pump 103 communicates fluidically with the saline tube 105.

Figure 11:
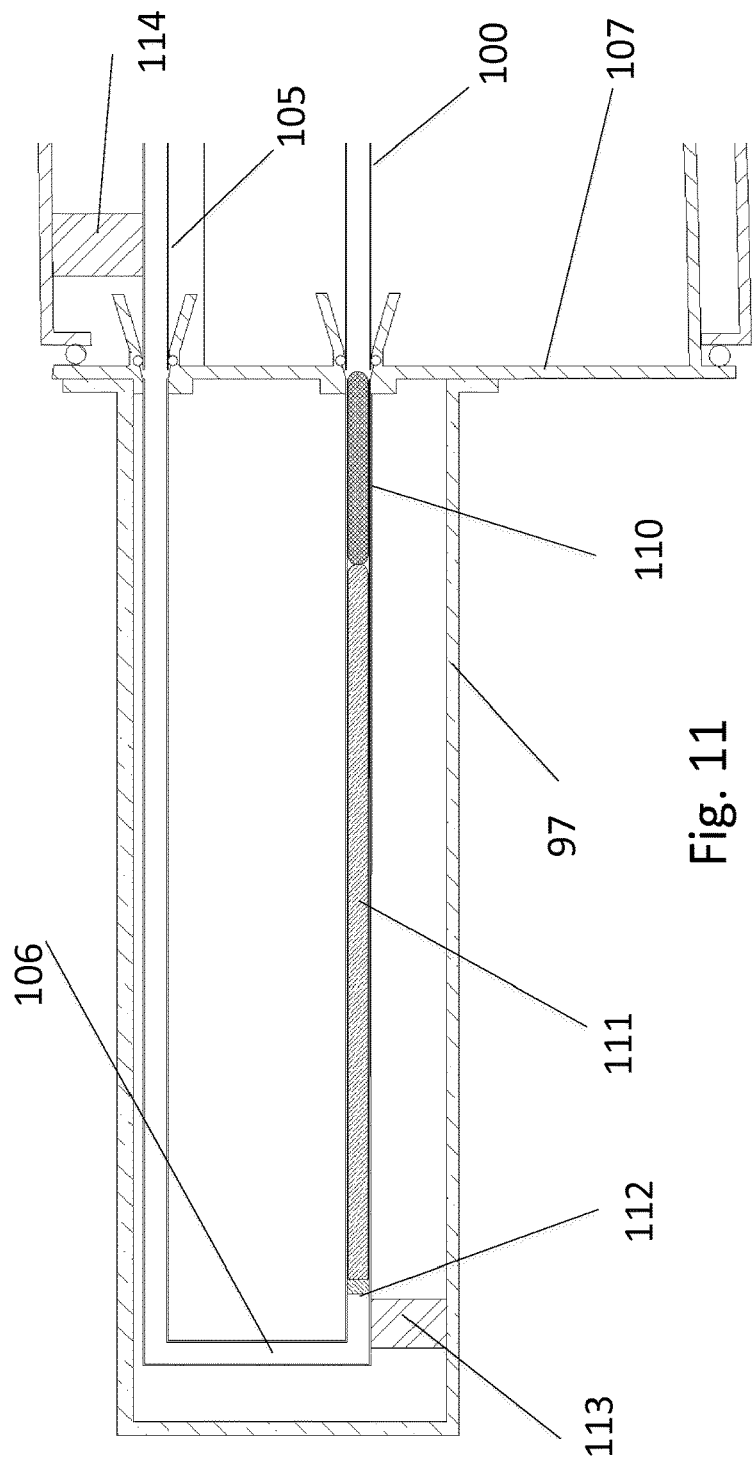
FIG. 11 is a close up of the marker tube from FIG. 10.

FIG. 11 is a close up of the marker tube from FIG. 10. The saline tube 105 is supported with tube support 114 connected to the basket case 108. The marker tube 106 is supported with tube support 113 connected to the basket cover 97. Shown inside the marker tube 106 in the storage position are the marker assembly 110, drive rod 111 and push plug 112.

It may be necessary to provide a slight press fit or light duty adhesive between the marker assembly 110 and the marker tube 106. It is important that the marker assembly 110 does not move out of position during handling or when the basket case 108 is evacuated. This slight press fit or light duty adhesive would be overcome by the force of the saline pressure on the push plug 112.

Figure 12:
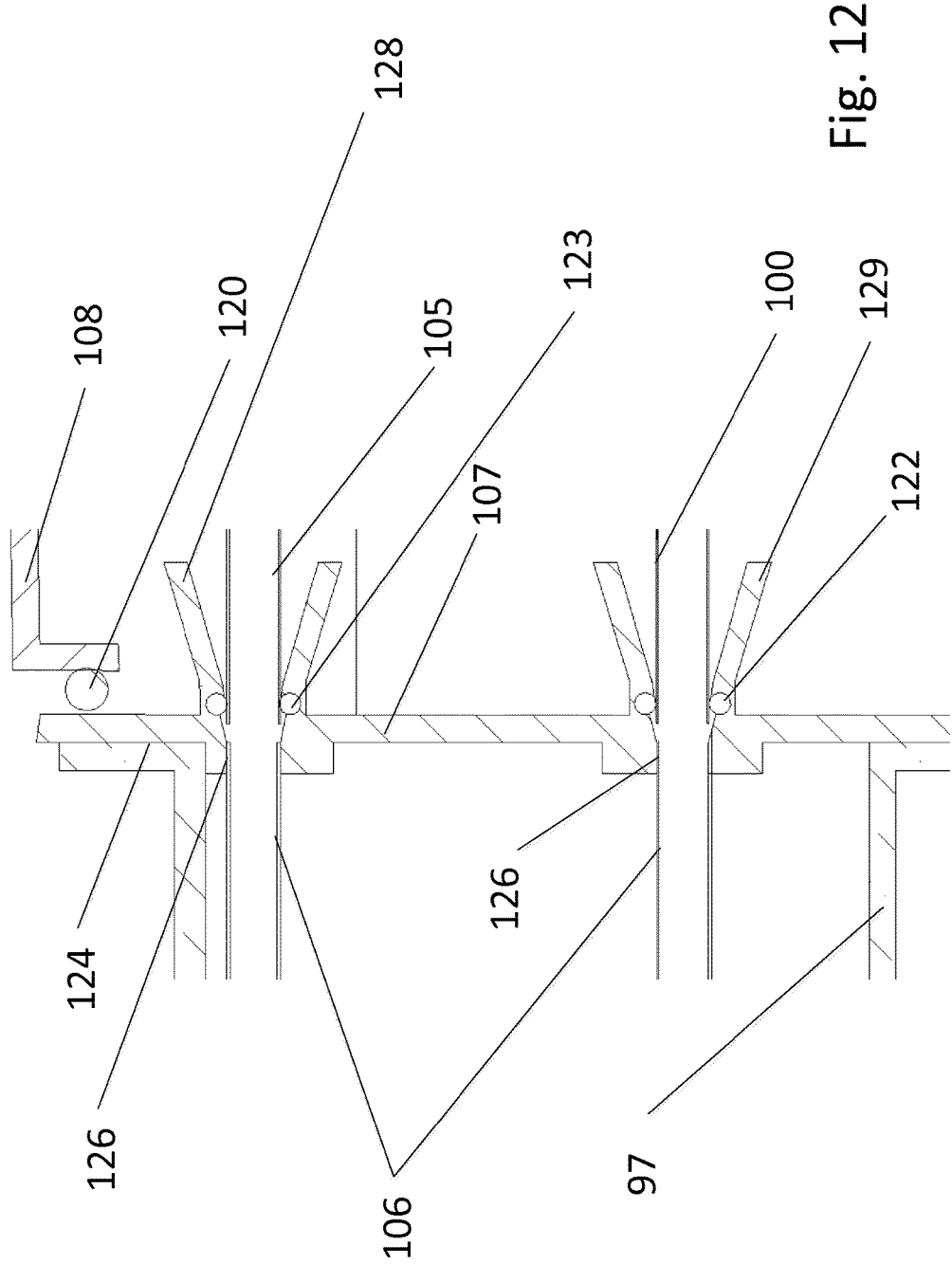
FIG. 12 is a close up of the cutter tube to marker tube connection taken from FIG. 11.

FIG. 12 is a close up of the cutter tube to marker tube connection taken from FIG. 11. This connection allows the basket 107 to be separated from the basket case 108. The basket seal 120 is an elastomeric material and maintains the vacuum function across the basket case 108 to basket 107 interface. The tube seal 123 is an elastomeric material and maintains the saline pressure function across the saline tube 105 to basket 107 interface. The tube seal 122 is an elastomeric material and maintains the saline pressure function across the cutter tube 100 to basket 107 interface. The tube weld 126 (two places) maintains the saline pressure function across the market tube 106 to basket 107 interface. The tube weld 126 is a permanent connection such as spin weld, adhesive or press fit. The basket cover weld 124 is a connection between the basket 107 and the basket cover 97. The basket cover weld 124 is a permanent connection such as vibration weld, adhesive or fasteners.

The lead in ramps 128-129 facilitate the location of the saline tube 105 and cutter tube 100 when the basket 107 is assembled to the basket case 108. The lead in ramp 129 also facilitates the cutter tube 100 to basket 107 alignment when the cutter tube 100 is retracted (aperture 170 is opened).

Figure 13:
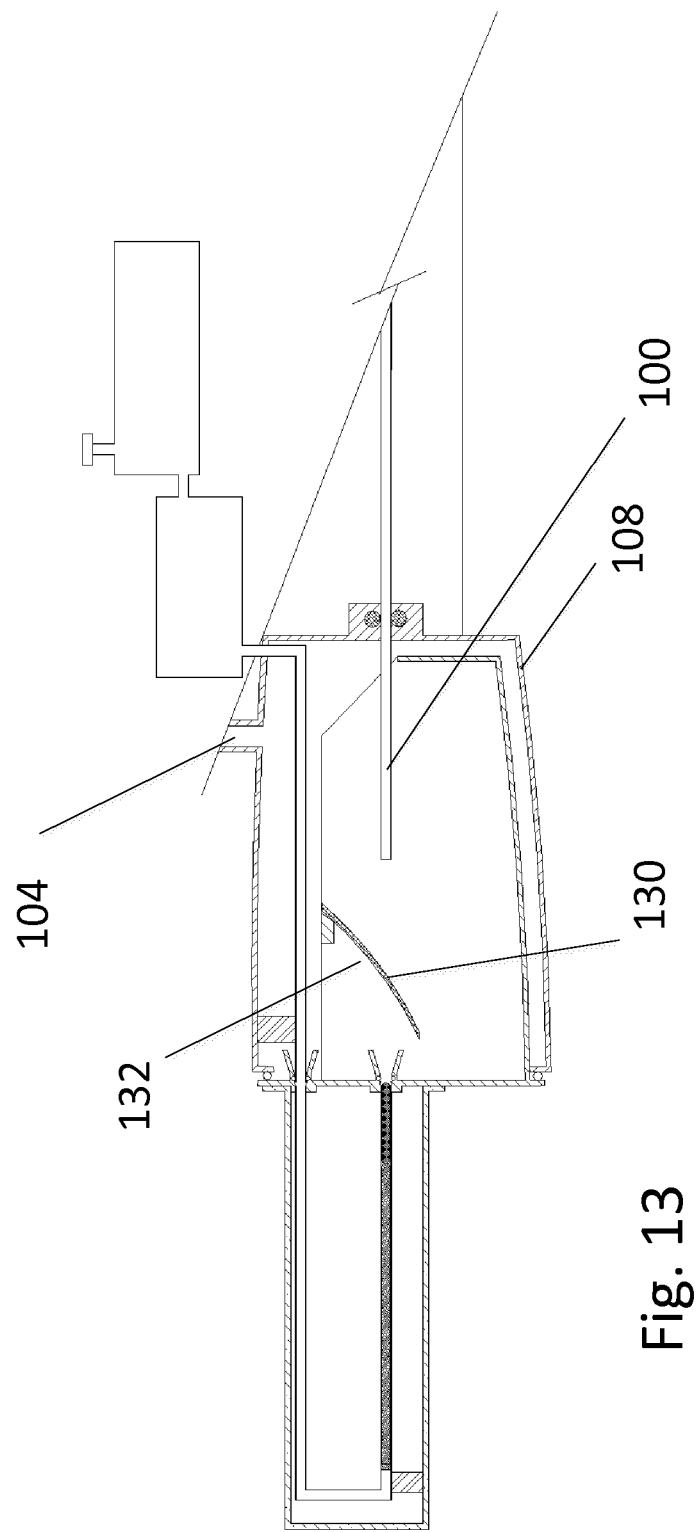
FIG. 13 is a section view of the handle end, after cutter tube forward travel, taken along section line A-A from FIG. 9.

FIG. 13 is a section view of the handle end, after cutter tube forward travel, taken along section line A-A from FIG. 9. In this view the cutter tube 100 is in the full forward position (aperture 170 is closed). The flap 130 is an elastomeric material and is attached to the flap bar 132 which is part of the basket 107.

In biopsy operation, this is the position just as the tissue sample 140 has been cut. The tissue sample 140 would still be near the needle tip 95. The vacuum port 104 would evacuate the basket case 108 and cause the tissue sample 140 to move through the cutter tube 100.

The purpose of the flap 130 is to keep the tissue sample 140 away from the lead in ramp 129.

Figure 14:
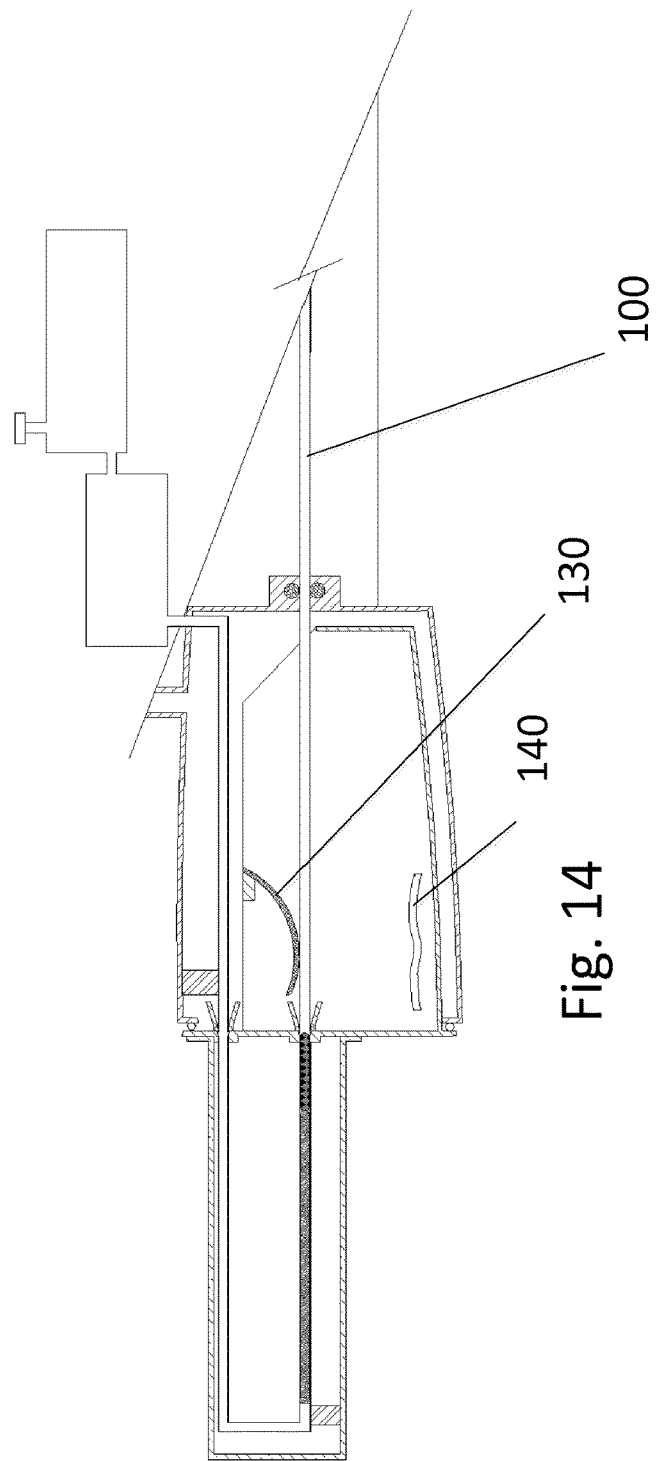
FIG. 14 is a section view of the handle end, after cutter tube retraction, taken along section line A-A from FIG. 9.

FIG. 14 is a section view of the handle end, after cutter tube retraction, taken along section line A-A from FIG. 9. The tissue sample 140 has been deposited in the basket 107. The cutter tube 100 has then been fully retracted and is properly seated to tube seal 122.

Figure 15:
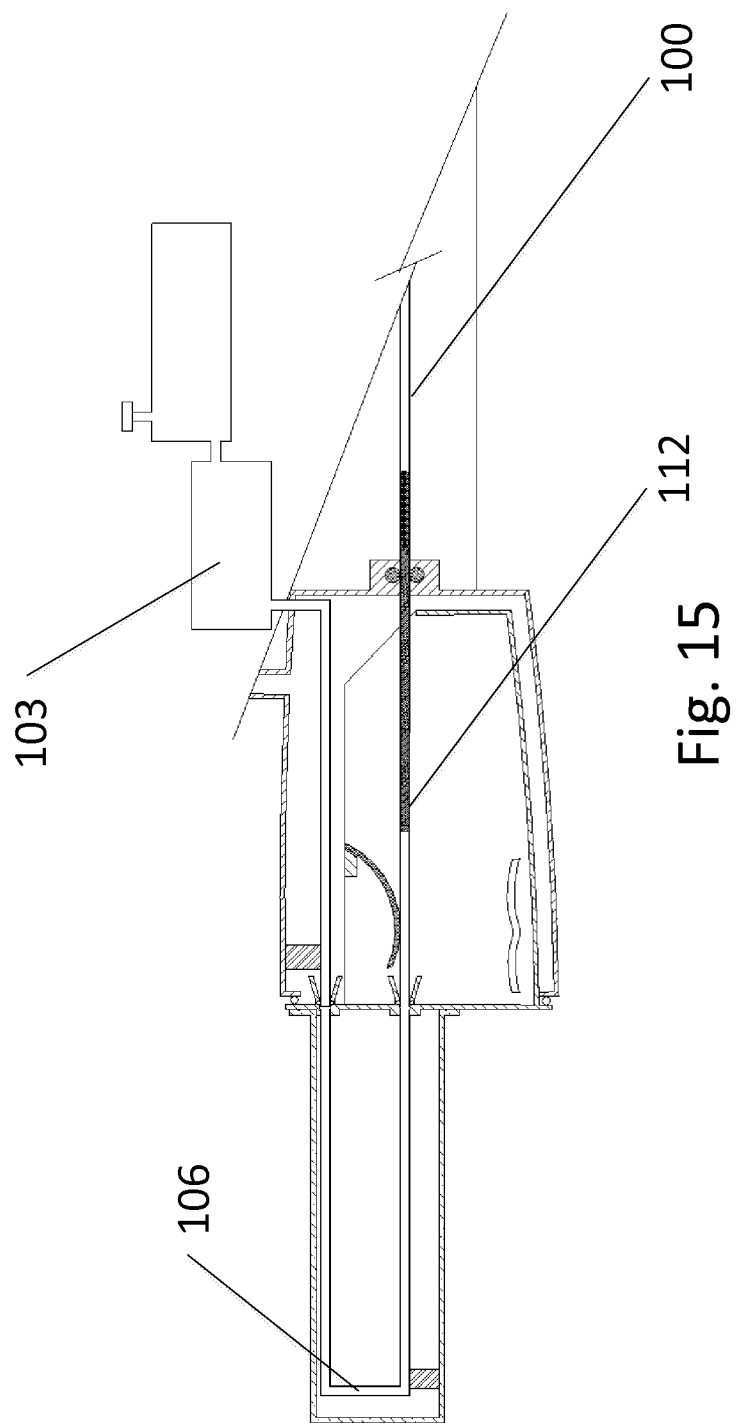
FIG. 15 is a section view of the handle end, as the drive rod movement begins, taken along section line A-A from FIG. 9.

FIG. 15 is a section view of the handle end, as the drive rod movement begins, taken along section line A-A from FIG. 9. To cause the marker deployment operation to start, the device would have already collected the tissue sample 140. The aperture 170 would still be closed. The doctor would manually retract the needle assembly 91 about 10 mm. This distance is approximately one half of the aperture 170 length. This will allow the marker assembly 110 to exit the aperture 170 at the midpoint of the tissue sample 140 extraction location. The doctor would now press the "marker deploy" button on the handle assembly 93. The following steps would happen automatically and controlled by the handle assembly 93 micro controller.

a. The cutter tube 100 would fully retract.
   b. The saline pump 103 would be energized.
   c. The saline tube 105 would be pressurized.
   d. The marker tube 106 would be pressurized in the area behind the drive plug 112.
   e. The saline pressure would cause the drive plug 112 to move inside the marker tube 106.

f. As the saline plug 112 moves, it will cross over from the marker tube 106 to the cutter tube 100.

g. The cutter tube 100 would be pressurized in the area behind the drive plug 112.

The saline pressure could be as high as needed to cause the required motion of the drive rod 111. At least 100 kPa would be needed to overcome the marker assembly 110 adhesion to resist evacuation force. It is anticipated that a saline pressure minimum of 200 kPa would be used. As much as 2000 kPa could be generated by the saline pump 103 to cause the required motion of the drive rod 111.

Figure 16:
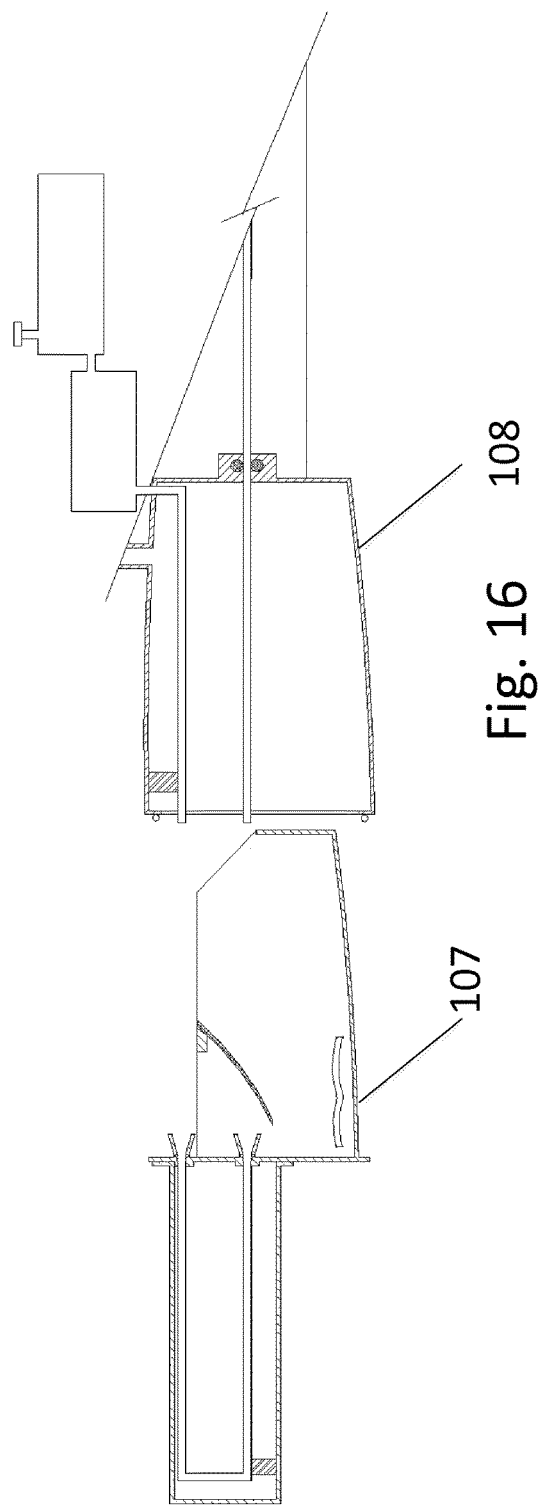
FIG. 16 is a section view of the handle end, with basket removed, taken along section line A-A from FIG. 9.

FIG. 16 is a section view of the handle end, with basket removed, taken along section line A-A from FIG. 9. This view is after the marker assembly 110 has been deployed. The basket 107 has been removed from the basket case 108 to allow access to the tissue sample 107. The basket 107 is releasably connected to the basket case 108 with a device such as the basket release 57.

Figure 17:
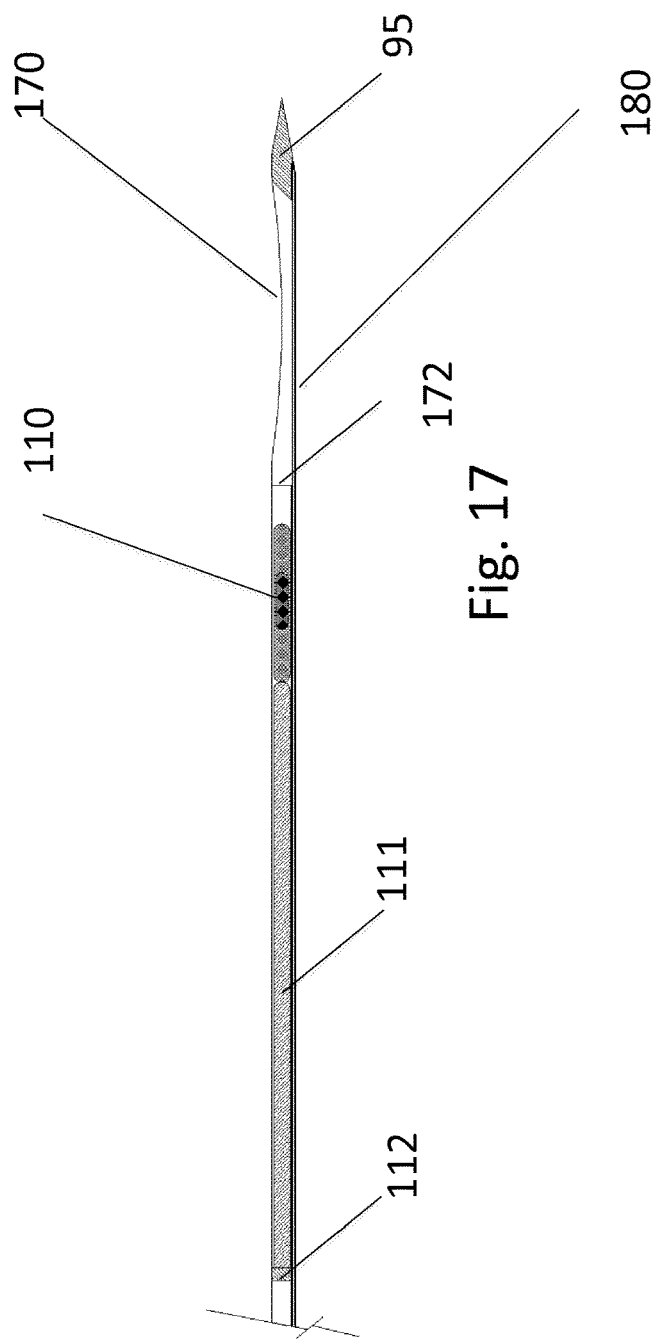
FIG. 17 is a section view of the needle end, with drive rod in mid movement, taken along section line A-A from FIG. 9.

FIG. 17 is a section view of the needle end, with drive rod in mid movement, taken along section line A-A from FIG. 9. In this view the saline pressure behind the push plug 112 has caused further movement down the cutter tube 100. The movement of the push plug 112 has caused the push rod 111 and the marker assembly 110 to also move. The marker assembly 110 is close to moving out the end of cutter tube 172.

The cutter tube 100 slides inside the needle tube 180. The aperture 170 is an opening in the needle tube 180. The needle tip 95 is permanently connected to the needle tube 180 with attachment means such as weld, adhesive, press fit, solder or braze.

Figure 18:
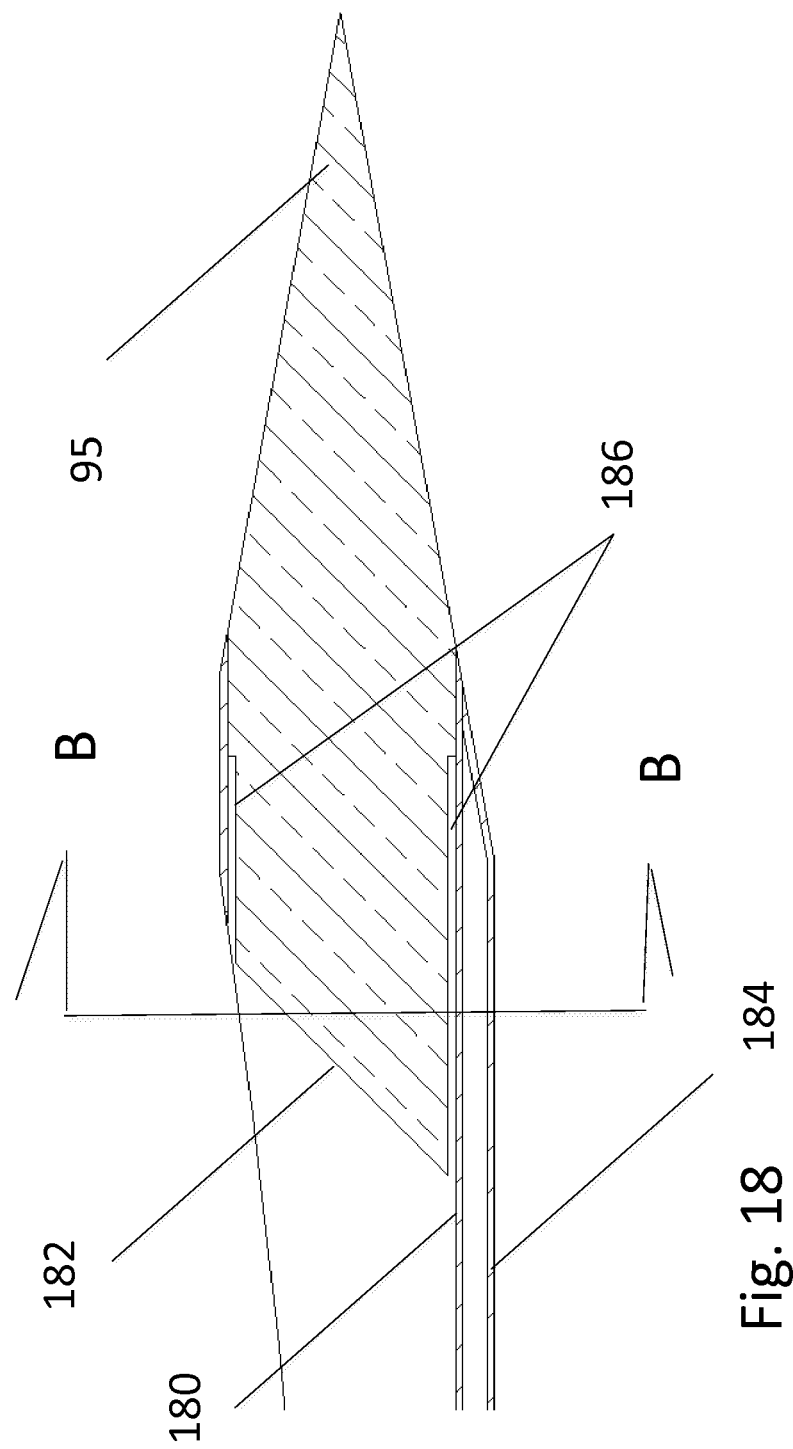
FIG. 18 is a close up of the needle tip taken from FIG. 17.

FIG. 18 is a close up of the needle tip taken from FIG. 17. The vacuum tube 184 is permanently connected to the needle tube 180 with attachment means such as weld, adhesive, solder or braze. There are openings between the needle tube 180 lumen and vacuum tube 184 lumen in the vicinity of the aperture 170.

The ramp 182 causes the marker assembly 110 to deploy from the aperture 170. The cutter tube pocket 186 exists between the needle tip 95 and the needle tube 180. It is important that the cutter tube pocket 186 extends past the aperture 170 opening to allow the cutter tube 100 to fully sever the tissue sample 140. It is also important that the ramp 182 be far enough toward the handle assembly 93 that the marker assembly 110 does not contact the aperture 170 opening as it exits. The start of the ramp 182 surface needs to be low enough in the needle tube 180 (away from the aperture 170) to cause the marker assembly 110 to move up toward the aperture 170. This means that the start of the ramp 182 should be below the nose radius of the marker assembly 110.

The ramp 182 is shown as a single plane. However, this ramp 182 surface could be more than one plane, one or more curved surfaces, or any combination of surfaces.

The ramp 182 is shown as being part of the needle tip 95. As an alternate construction, the ramp 182 could be incorporated into a separate part that is attached to either the needle tip 95, needle tube 180 or vacuum tube 184.

Figure 19:
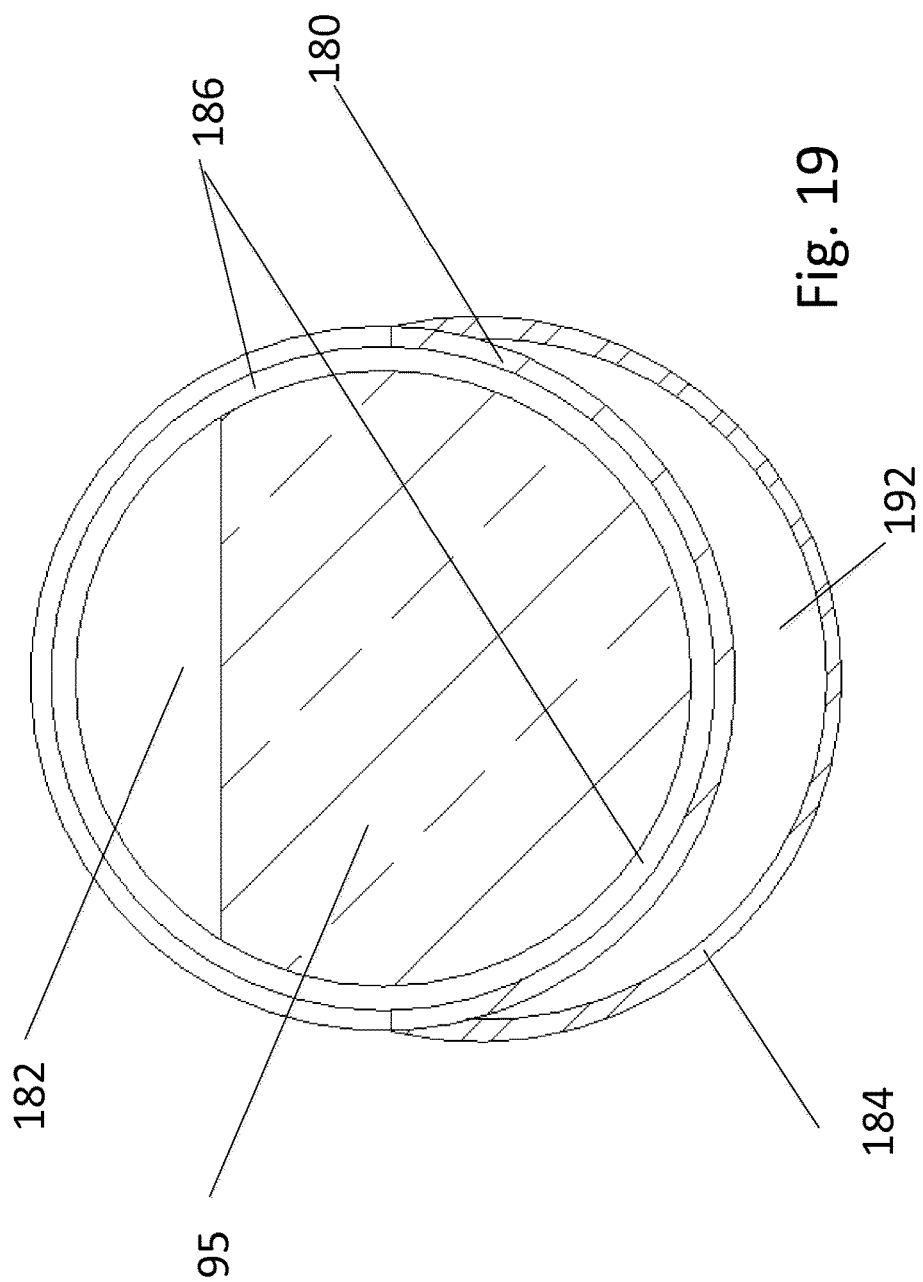
FIG. 19 is a section view of the needle tip, taken along section line B-B from FIG. 18.

FIG. 19 is a section view of the needle tip, taken along section line B-B from FIG. 18. This view shows the vacuum lumen 192 and cutter tube pocket 186. The cutter tube pocket 186 is a full circle due to the rotation and translation of the cutter tube. The section line B-B was chosen part way up the ramp 182 surface. Part of the ramp 182 surface is visible behind the sectioned needle tip 95.

Figure 20:
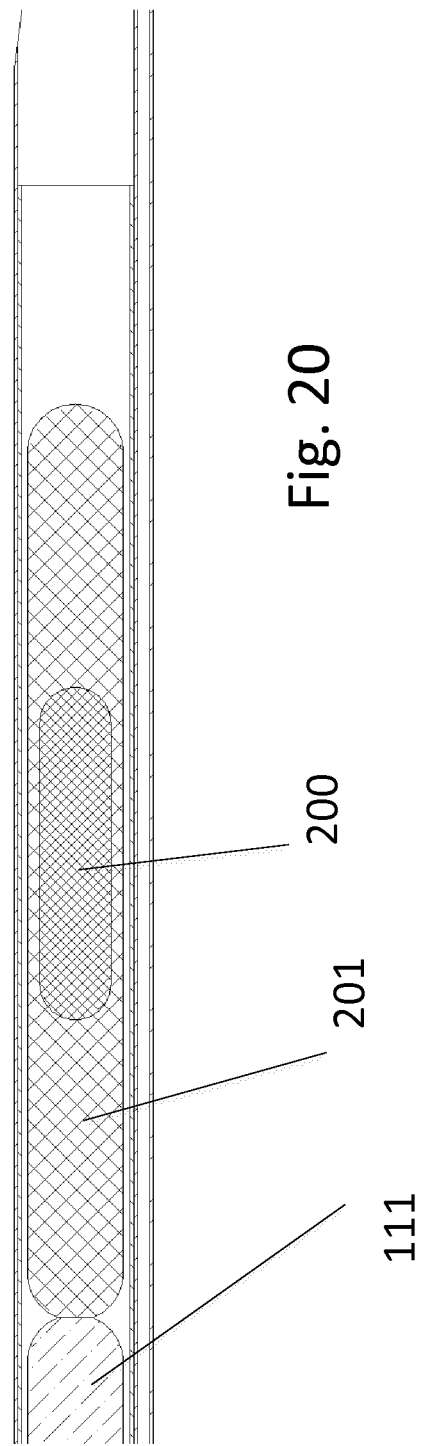
FIG. 20 is a close up of the marker assembly taken from FIG. 17.

FIG. 20 is a close up of the marker assembly taken from FIG. 17. The marker assembly 110 includes a marker clip 200 and pledget 201. The marker clip 200 is opaque to visual scanning methods and is also referred to as the biopsy marker. The pledget 201 surrounds the marker clip 200 and facilitates the implatation of the marker clip 200 to the surrounding tissue.

The leading edge radius of the pledget 201 facilitates smooth transition of movement between the marker tube 106 and cutter tube 100. The leading edge radius of the pledget 201 also facilitates the ramp 182 directing of the pledget 201 toward the aperture 170. The leading edge radius of the drive rod 111 facilitates smooth transition of movement between the marker tube 106 and cutter tube 100. As an alternate construction, it may be useful for the leading edge of the drive rod 111 to have a combination of flat, chamfer, radius and/or compound curve. This more complicated shape may facilitate the jamming of the drive rod 111 against the ramp 182.

Figure 21:
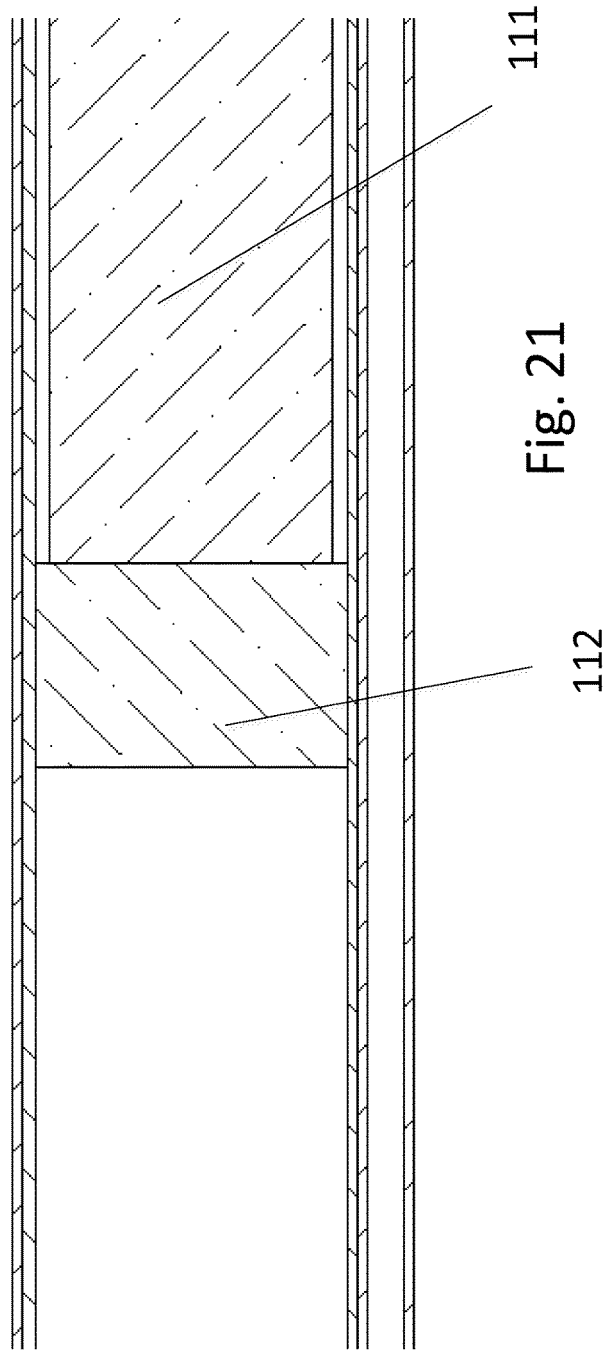
FIG. 21 is a close up of the drive plug taken from FIG. 17.

FIG. 21 is a close up of the drive plug taken from FIG. 17. The drive plug 112 is made of an elastomeric material. The purpose of the drive plug 112 is to seal the saline pressure against the marker tube 106 and cutter tube 100. It is important that the drive plug 112 be long enough to bridge the gap between marker tube 106 and cutter tube 100. Although not shown in FIG. 21, it may be useful for the drive plug 112 to have a leading edge radius or chamfer to facilitate smooth transition of movement between the marker tube 106 and cutter tube 100. It may also aid in alignment and smooth operation for the drive plug 112 to be attached to the drive rod 11.

Figure 22:
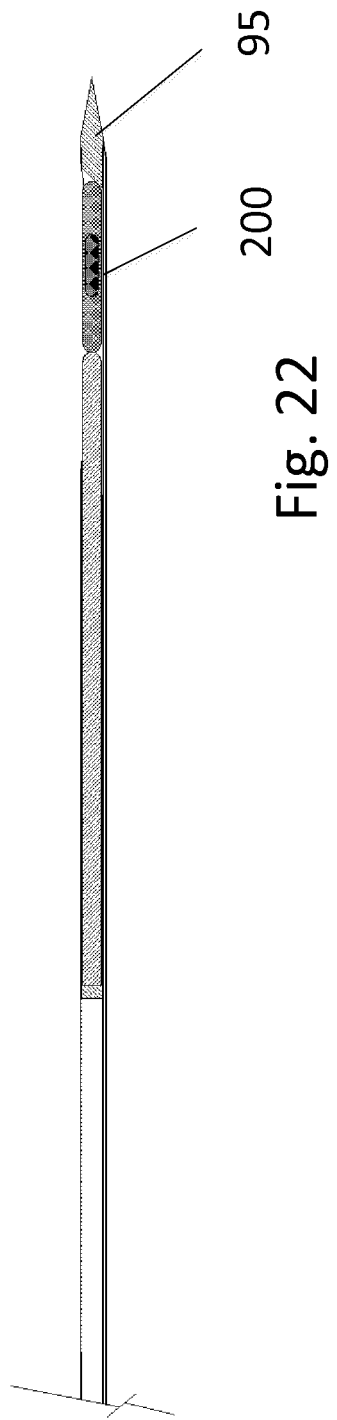
FIG. 22 is a section view of the needle end, when marker assembly contacts ramp, taken along section line A-A from FIG. 9.

FIG. 22 is a section view of the needle end, when marker assembly contacts ramp, taken along section line A-A from FIG. 9.

Figure 23:
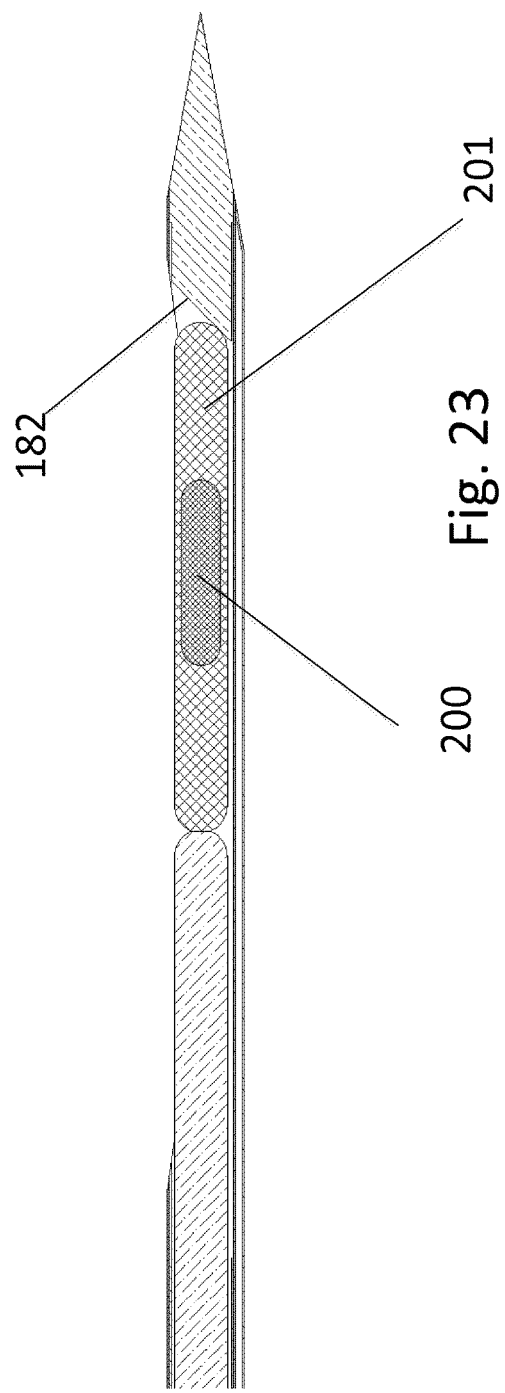
FIG. 23 is a close up of the marker assembly taken from FIG. 22.

FIG. 23 is a close up of the marker assembly taken from FIG. 22. Note the approximate 45 degree contact angle between the ramp 182 and the leading edge of the pledget 201. This contact angle causes the leading edge of the pledget 201 to be directed toward the aperture 170.

Figure 24:
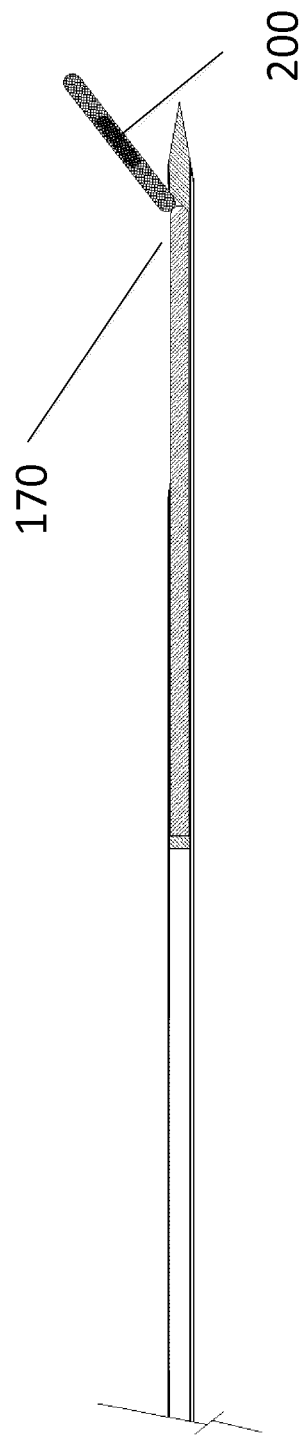
FIG. 24 is a section view of the needle end, when drive rod contacts ramp, taken along section line A-A from FIG. 9

FIG. 24 is a section view of the needle end, when drive rod contacts ramp, taken along section line A-A from FIG. 9. The drive rod 111 is at the end of forward translation and the marker clip 200 is fully out of the aperture 170.

Figure 25:
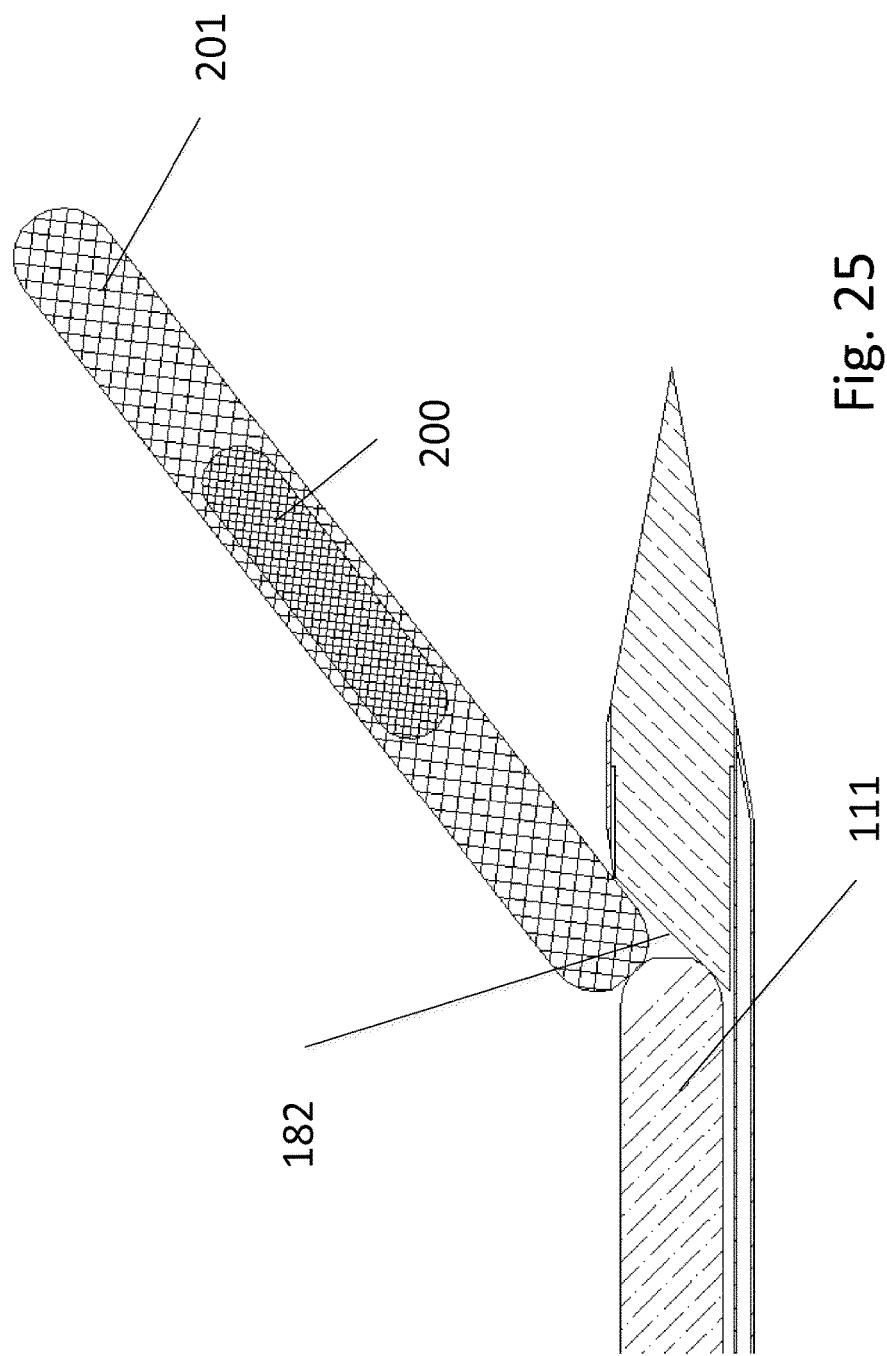
FIG. 25 is a close up of the marker assembly taken from FIG. 24.

FIG. 25 is a close up of the marker assembly taken from FIG. 24. The drive rod 111 contacts the ramp 182. The drive rod 111 is made of a strong and stiff material such as stainless steel. The ramp 182 causes a bending moment on the drive rod 111 which is resisted by the trailing portion of the drive rod 111 remaining inside the cutter tube 100. This will cause the drive rod 111 to bend slightly toward the aperture 170 and jam in place. This position of the drive rod 111 is useful to mostly cover the aperture 170 in preparation for needle assembly 91 retraction.

This view shows the pledget 201 in an approximately 45 degree position in the tissue sample 140 extraction location. In practice, the tissue surrounding the tissue sample 140 extraction location would cause the pledget 201 to exit the aperture 170 and position more aligned with the axis of the drive rod 111 motion.

Step (h) from the FIG. 15 description would now be completed by the doctor. The needle assembly 91 would be manually refracted fully from the patient. As the needle assembly 91 is retracted, if a small portion of the trailing end of the pledget 201 remains in the aperture 170, it would be pushed away into the tissue sample 140 extraction location.

Figure 26:
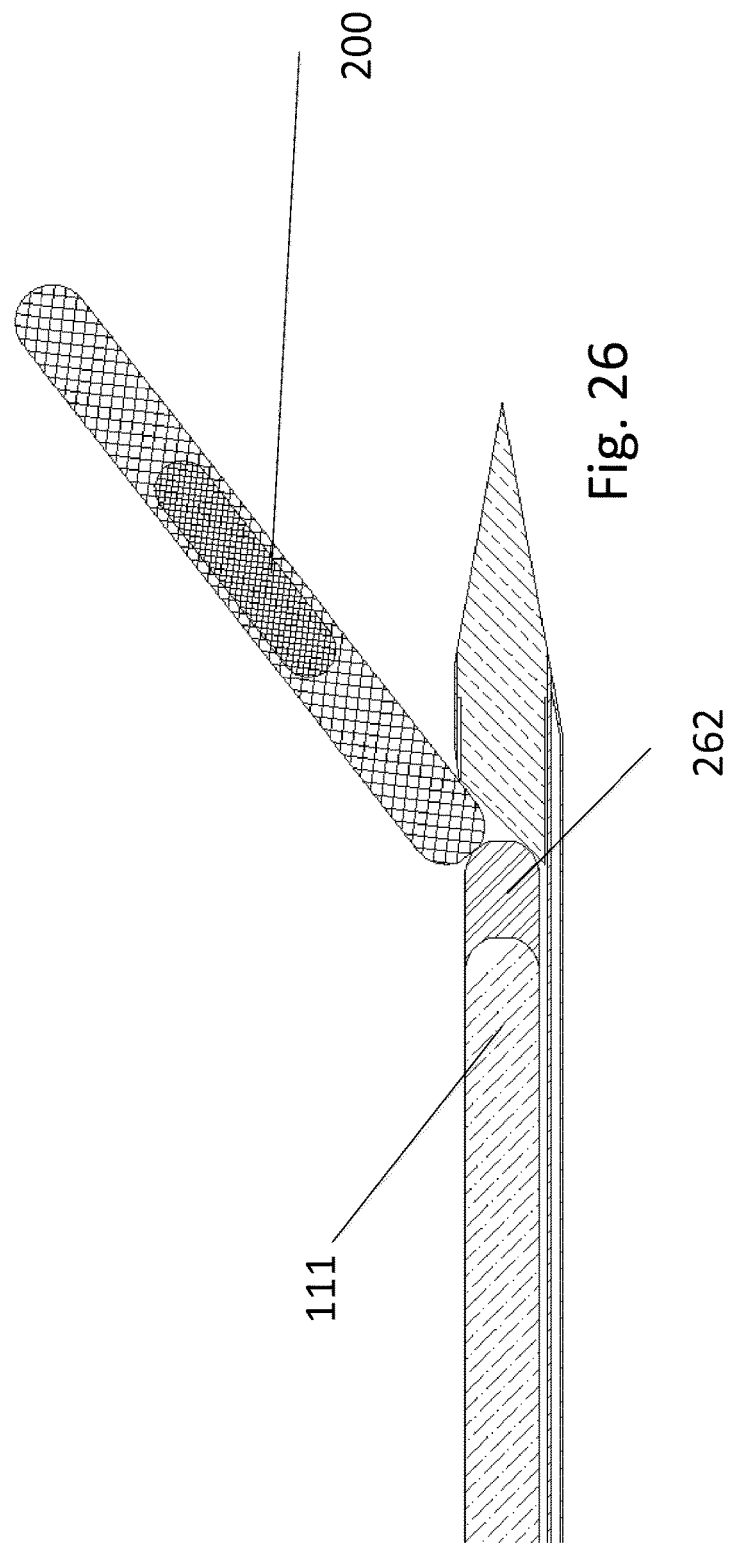
FIG. 26 is an alternate construction of the drive rod, same perspective as FIG. 25.

FIG. 26 is an alternate construction of the drive rod, same perspective as FIG. 25. As shown in FIG. 25, a slight amount of aperture 170 near the ramp 182 may still be exposed during needle assembly 91 withdrawal. This could potentially catch on patient tissue.

The rod tip 262 is made from a deformable material and affixed to the drive rod 111.

Figure 27:
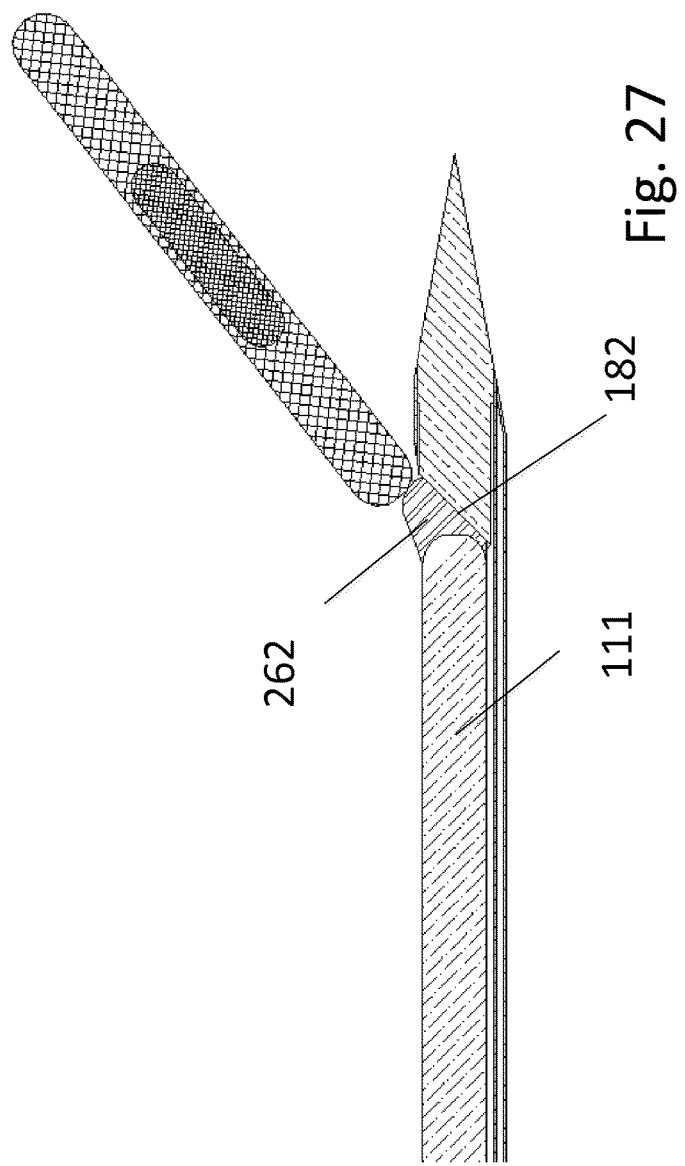
FIG. 27 is an alternate construction of the drive rod, same perspective as FIG. 26 after forward motion stops.

FIG. 27 is an alternate construction of the drive rod, same perspective as FIG. 26 after forward motion stops. The rod tip 262 severely deforms between the ramp 182 surface and the drive rod 111. The rod tip 262 material would be such that springback would be minimized and it would remain in the deformed condition. With this alternate construction the aperture 170 is now fully covered during needle assembly 91 withdrawal.

Figure 28:
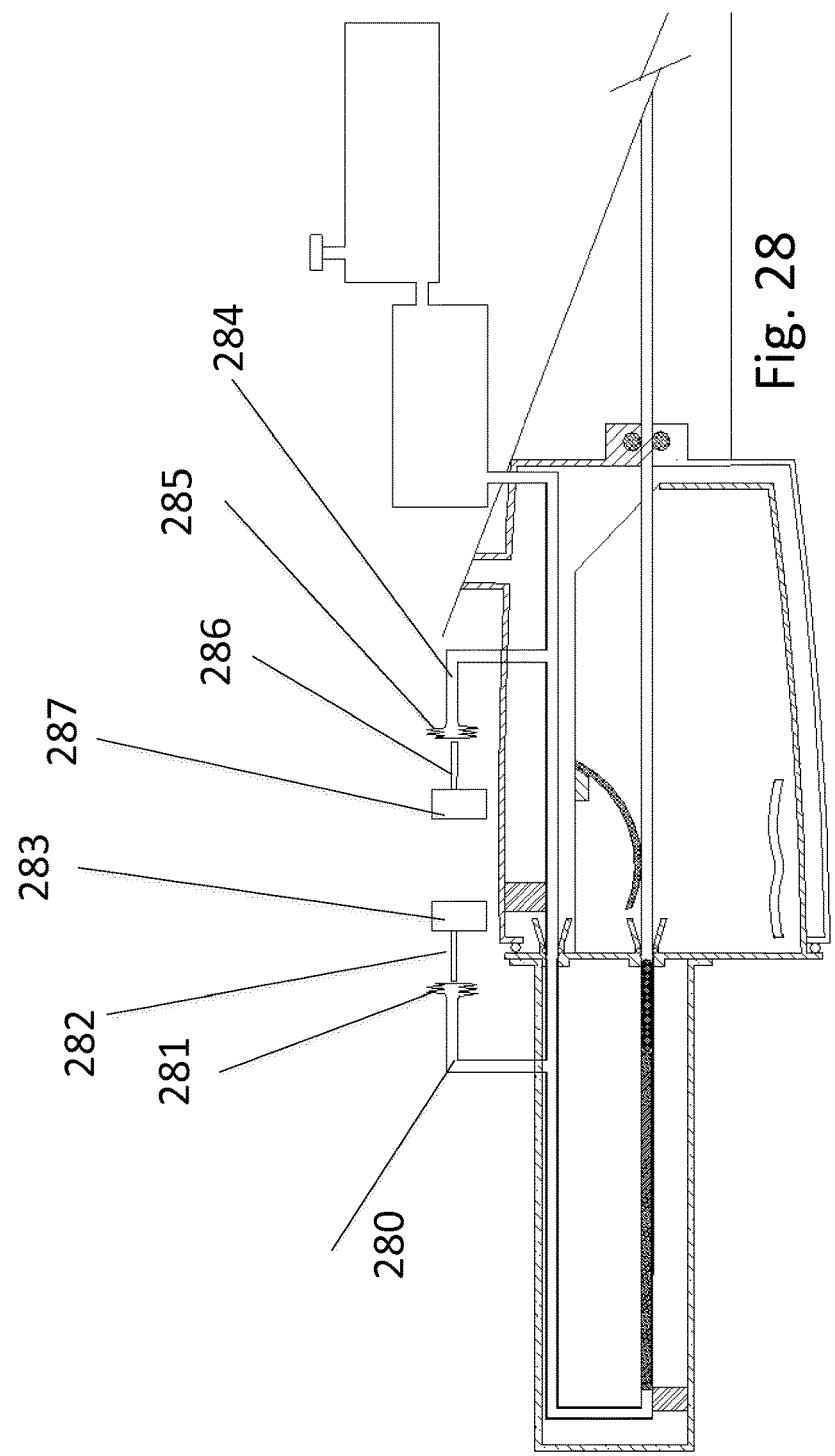
FIG. 28 is a section view of the handle end, with pressure sense original, taken along section line A-A from FIG. 9.

FIG. 28 is a section view of the handle end, with pressure sense original, taken along section line A-A from FIG. 9. It would be useful for the doctor to have indicator lights on the handle assembly 93 during operation. The rod sense tube 284 communicates the saline pressure to the rod bellows 285. The rod bellows 285 is a device which extends under fluid pressure but does not retract after the pressure is released. The rod bellows 285 material would be a stainless steel material with low spring back.

The marker sense tube 280 communicates the saline pressure to the marker bellows 281. The marker bellows 281 would operate similar to the rod bellows 285.

The two bellows 281, 285 are shown in the position for a new unused device ready for a procedure to begin. Note the drive rod 111 is in the stored position in the marker tube 106.

Figure 29:
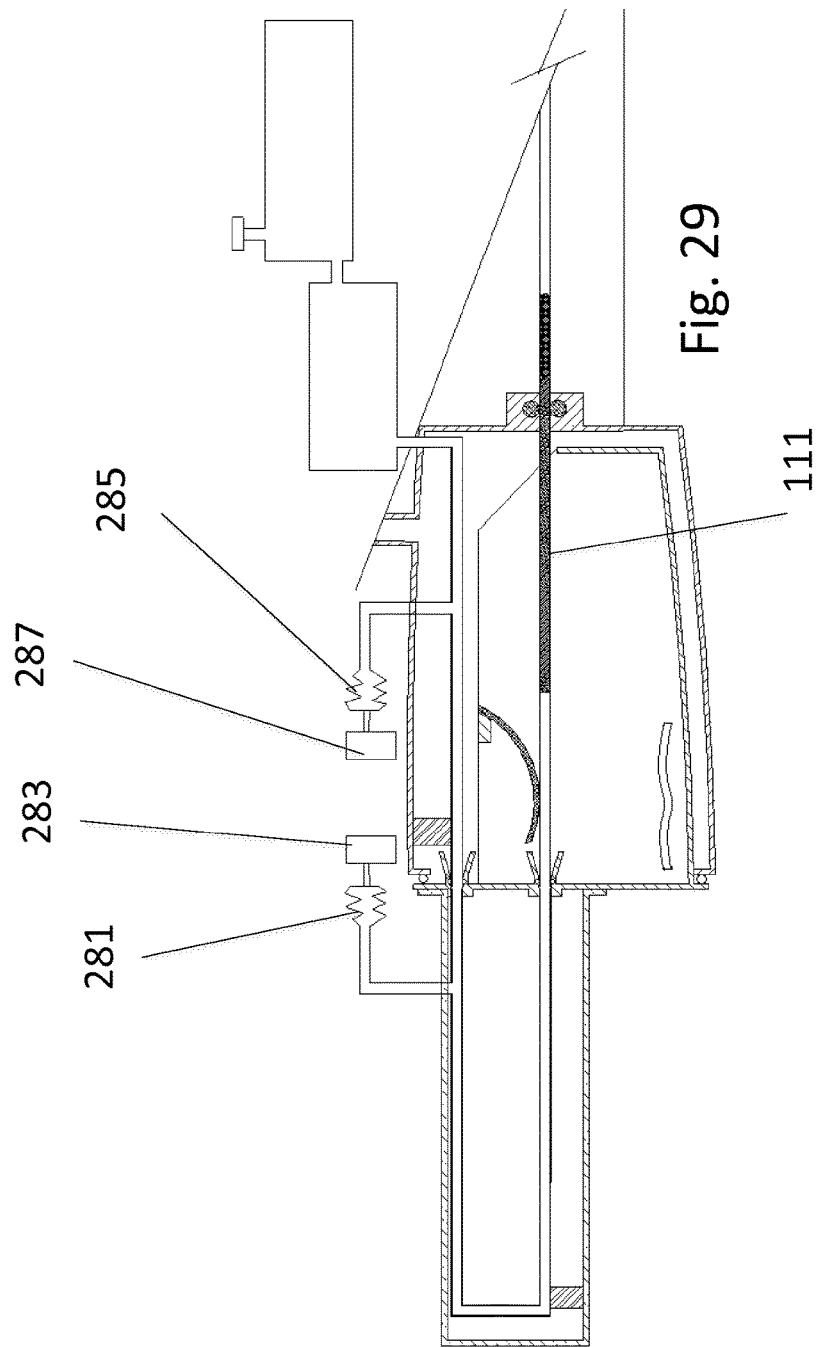
FIG. 29 is a section view of the handle end, with pressure sense confirmed, taken along section line A-A from FIG. 9.

FIG. 29 is a section view of the handle end, with pressure sense confirmed, taken along section line A-A from FIG. 9. Note the drive rod 111 has been pushed out of the marker tube 106 due to saline pressure and will be jammed into the ramp. The rod bellows 285 sensed this saline pressure and moved to the extended position. In this position, the rod bellows 285 contacts the rod switch plunger 286 and actuates the rod switch 287. The rod switch 287 communicates with the handle assembly 93 micro controller. The micro controller would display that the drive rod 111 is jammed against the ramp 182. In operation, this would confirm to the doctor that the marker assembly 110 has deployed. If the rod switch 287 was sensed as actuated at the start of a procedure, the handle assembly 93 micro controller would display an error code and prevent further operation. This could happen if a second procedure was attempted without changing to a new needle assembly 91.

The marker bellows 281 sensed the saline pressure and moved to the extended position. In this position, the marker bellows 281 contacts the marker switch plunger 282 and actuates the marker switch 283. The marker switch 283 communicates with the handle assembly 93 micro controller. The micro controller would display that the marker assembly 110 is missing from the basket 107. In operation, this would confirm to the doctor that the basket 107 no longer contains a marker assembly 110. If the marker switch 287 was sensed as actuated at the start of a procedure, the handle assembly 93 micro controller would display an error code and prevent further operation. This could happen if a procedure was attempted with a basket 107 that had previously been used for a marker assembly 110 deployment.

An alternate construction for the marker bellows 281 or rod bellows 285 would be to use a bellows made of an elastomeric material. The motion of the bellows could be captured with a latching lever. This lever would then provide the switch action after the saline pressure is released.

As a control enhancement, it would be useful if the handle assembly 93 micro controller would prevent a marker assembly 110 deployment until after a tissue sample 140 has been obtained.

It is desirable to have several variations of marker clip 200 shape. This would be for personal doctor preference on visual scanning or if two or more tissue samples 140 are taken and the multiple tissue sample 140 extraction locations need to be differentiated.

The basket 107 is preloaded with marker clip 200 and the particular style of marker clip 200 would be identified on a visible location of the basket 107. The marker clip 200 style could be easily changed by exchanging the basket 107 in the needle assembly 91.

Figure 30:
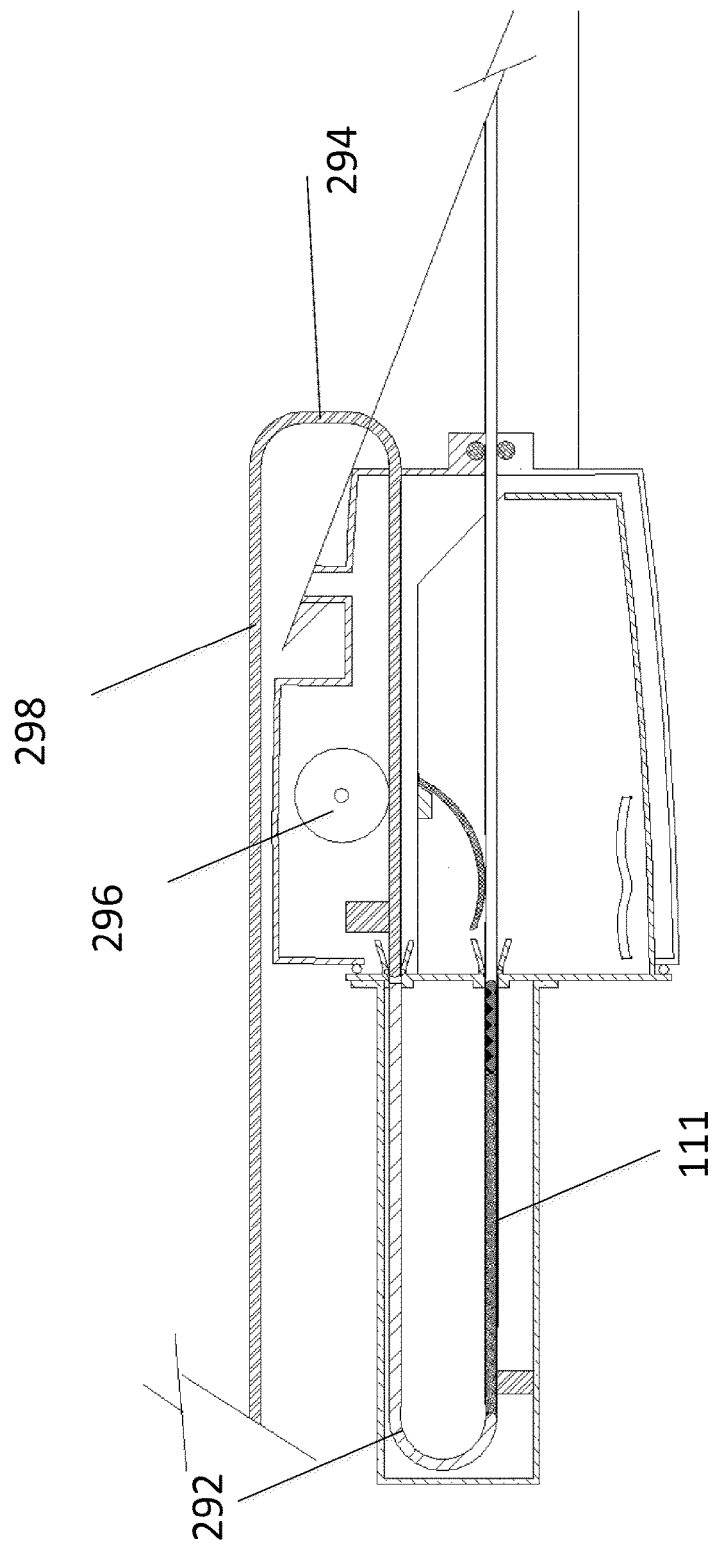
FIG. 30 is an alternate construction of the drive means, same perspective as FIG. 14.

FIG. 30 is an alternate construction of the drive means, same perspective as FIG. 14. In the storage position shown, the marker tube 106 contains the marker assembly 110, drive rod 111 and the cover rod 292. The drive plug 112 and all saline components have been eliminated. The push tube 298 contains the push rod 294. The push rod 294 would need to have a minimum length equal to the needle tip 95 to basket cover 97 dimension. The push tube 298 could be shorter than the push rod 294, with the exposed push rod 294 routed inside the needle assembly in such a manner as to not get hung up when pulled.

The push rod 294 and cover rod 292 would be made of semi flexible material. It would also be useful for the parts to be covered with a sterile stabile lubricant or the material to be self lubricating.

Figure 31:
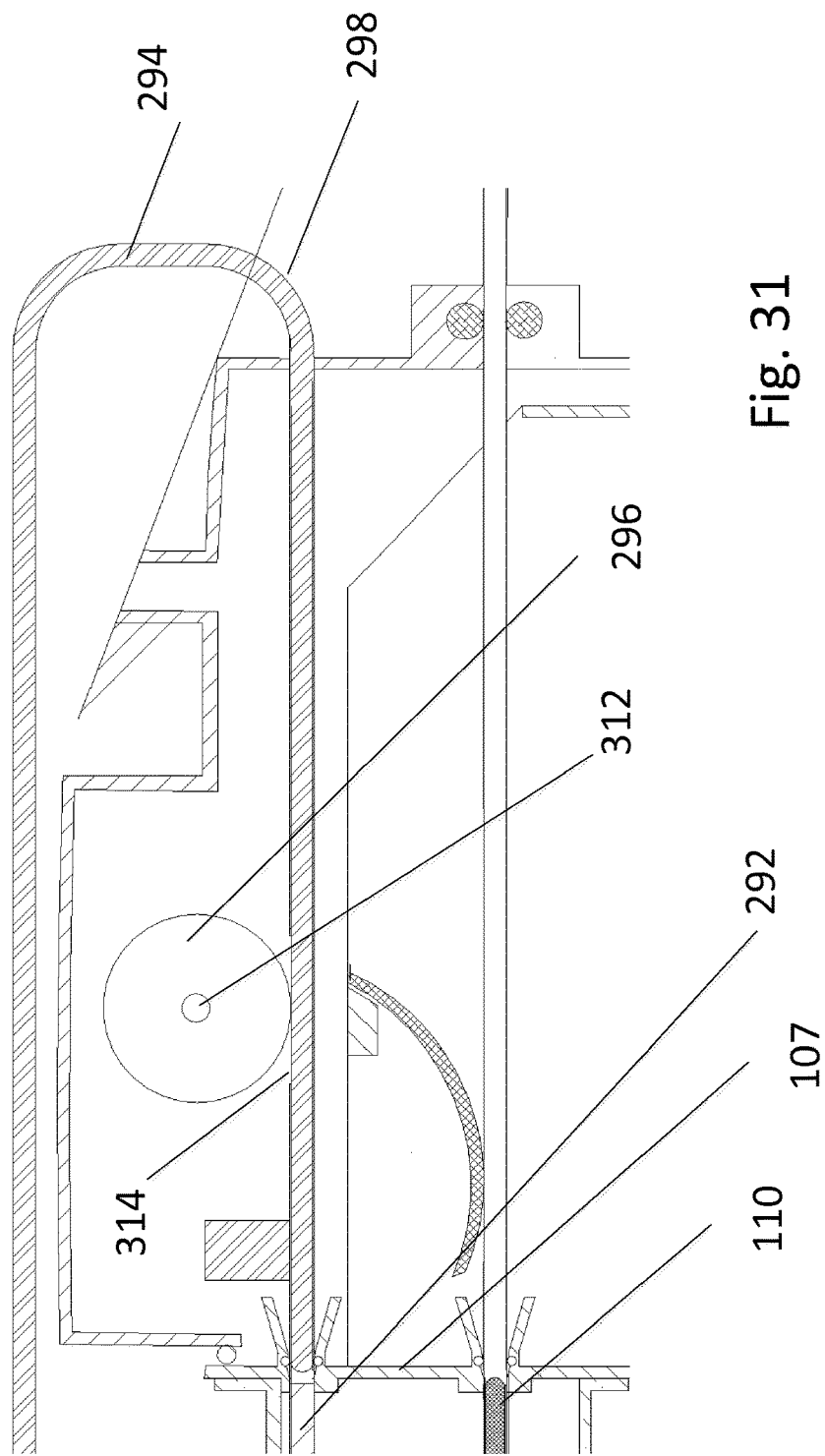
FIG. 31 is a close up of the drive means taken from FIG. 30.

FIG. 31 is a close up of the drive means taken from FIG. 30. The cover rod 292 to push rod 294 juncture at the basket 107 interface allows for basket 107 removal from the basket case 108. The push tube 298 has an opening 314 where the drive wheel 296 contacts the push rod 294. The rotation of the drive wheel 296 is caused by the drive wheel axle 312 which is connected to a drive wheel motor controlled by the handle assembly 93 micro controller.

A person skilled in the art would know of many design variations to mechanically cause linear motion of the push rod. Some possibilities include multiple drive wheels, serrations on the push rod with matching teeth on the drive wheel, or moving treads with idler wheels.

Figure 32:
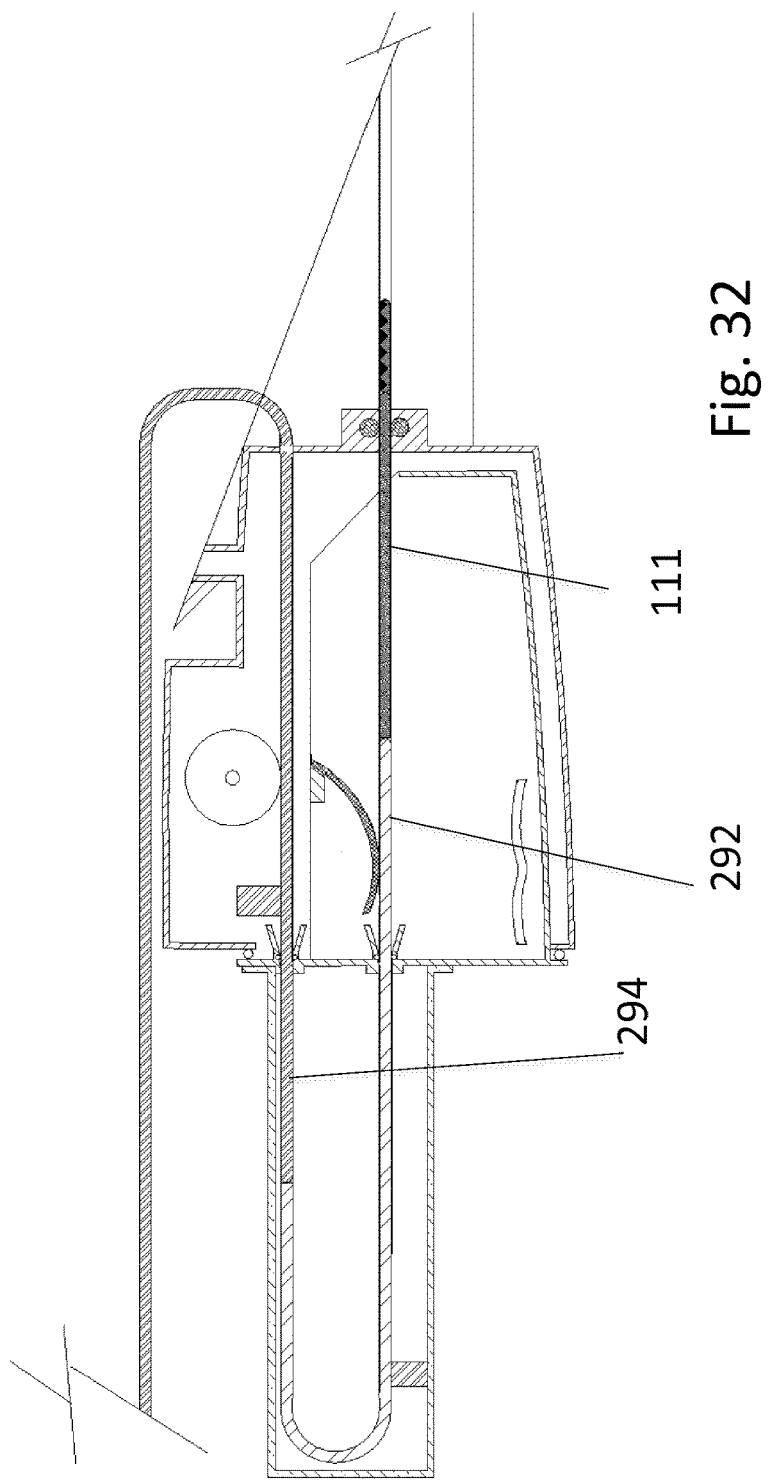
FIG. 32 is an alternate construction of the drive means after marker movement, same perspective as FIG. 14.

FIG. 32 is an alternate construction of the drive means after marker movement, same perspective as FIG. 14. The drive rod 111 has moved inside the cutter tube 100 and the push rod 294 has moved inside the marker tube 106. This motion would continue until the drive rod 111 contacts the ramp 182.

Figure 33:
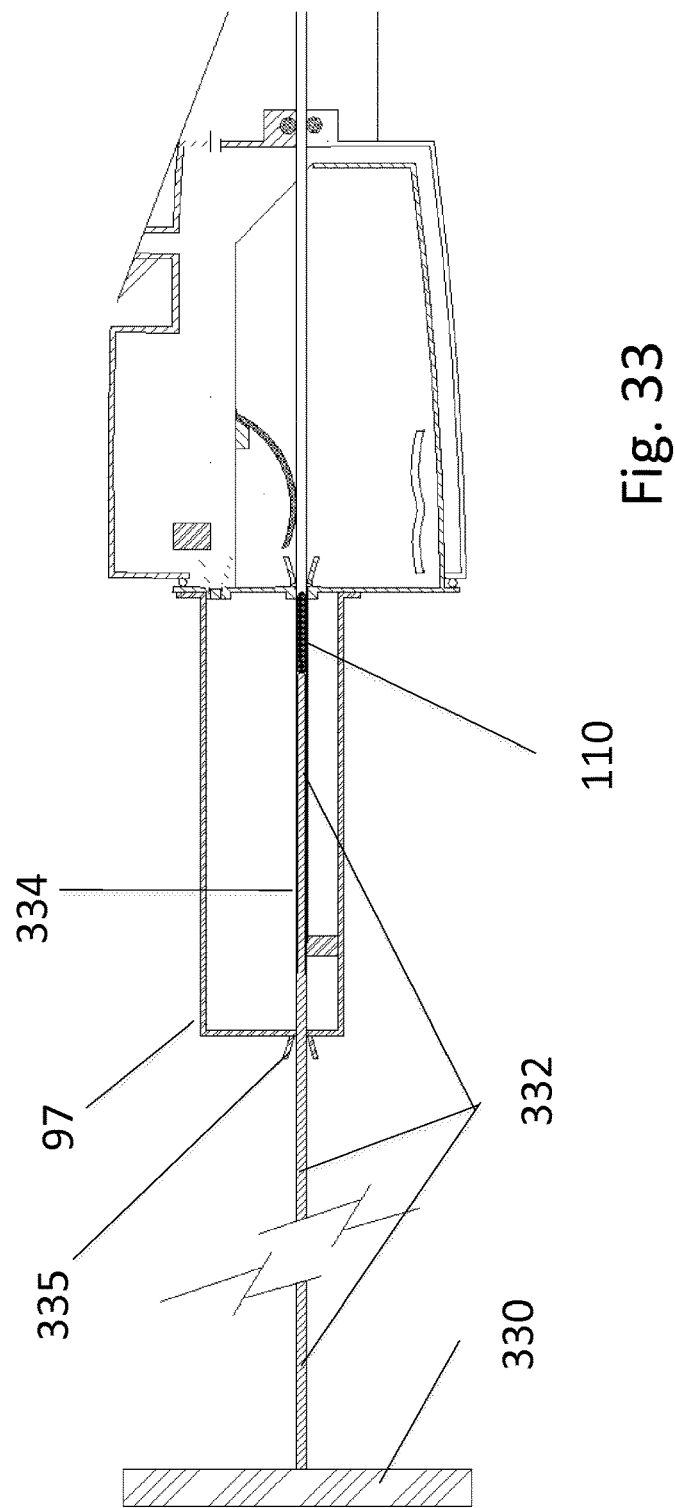
FIG. 33 is an alternate construction of a manual drive means, same perspective as FIG. 14.

FIG. 33 is an alternate construction of a manual drive means, same perspective as FIG. 14. The marker assembly 110 is the only component preinstalled in the manual tube 334. The manual tube 334 terminates at a hole at the rear of the basket cover 97. The basket cover includes lead in ramps 335 to facilitate insertion of the manual rod 332. The manual rod 332 would need to have a minimum length equal to the needle tip 95 to rear of basket cover 97 dimension. The manual rod 332 would be made from a material such as stainless steel.

In operation, after the tissue sample 140 is collected, the doctor would press the "aperture open" button. The handle assembly 93 micro controller would cause the cutter tube 100 to fully retract. The doctor would then manually insert the manual rod 332 into the basket cover 97 opening. The doctor would then manually advance the marker assembly 110 forward by pushing on the handle 330 which is connected to the manual rod 332. The forward motion would stop when the manual rod 332 tip struck the ramp 182 and the marker assembly 110 is deployed to the tissue sample 140 extraction location. The needle assembly 91 and manual rod 332 together would be withdrawn from the patient.

It may be desirable to reuse a needle assembly 91 with a drive rod 111 jammed against the ramp 182. A one time use sterile tool could be provided that is similar to the manual rod 332 except from a semi-flexible material. This tool could be inserted into the aperture 170 and used to push the drive rod 111 and drive plug 112 out the back of the cutter tube 100. The rod switch 287 would need an override capability. The needle assembly 91 could now be reused.

The saline pump 103 will need some time to build up to operational pressure. It may be desired to eliminate this delay. A spring loaded diaphragm or bladder could be located at the outlet of the saline pump 103. A solenoid valve could then be connected between the spring loaded diaphragm or bladder to the saline tube 105. The handle assembly 93 micro controller could energize the saline pump 103 as part of the operation warm up. The operational pressure would now be available without delay. The handle assembly 93 micro controller would energize the solenoid at the proper time to immediately pressurize the saline tube 105.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawings and description in this disclosure are provided to help the reader understand the invention, and do not limit the scope of the claims.

The invention claimed is:

1. A biopsy apparatus comprising:
a handpiece, wherein a needle extends distally from the handpiece;
the needle comprises a first lumen configured to receive a cutter, and a transverse aperture in fluid communication with the first lumen;
the cutter is translatable within the first lumen to sever a tissue protruding through the transverse aperture, wherein the cutter defines a second lumen;
a vacuum pump operable to draw the tissue proximally through the second lumen;
a marker positioned within a tube; means to push the marker out the transverse aperture;
the tube is axially aligned with the second lumen while the tissue is severed; and the tube is axially aligned and abutted with the cutter while the marker is pushed out the transverse aperture, and
wherein marker is axially aligned with the second lumen while the tissue is severed, while the tissue is drawn proximally through the second lumen, and while the the cutter while the tissue is severed.

2. The apparatus of claim 1 wherein the means to push the marker comprises a push rod, wherein the push rod extends outside the handpiece and opposite relative to the needle.

3. The apparatus of claim 1 wherein the means to push the marker comprises a pressure pump.

4. The apparatus of claim 3 wherein the biopsy apparatus is configured for one hand operation from when the tissue is severed through when the marker is pushed out the transverse aperture.

5. A biopsy apparatus comprising:
a needle comprising: a closed tip, a first lumen configured to receive a cutter, a transverse aperture in fluid communication with the first lumen, wherein the transverse aperture is proximal to the closed tip, an inclined surface at a distal end of a second lumen, wherein the inclined surface terminates at the transverse aperture;
a handpiece, wherein the needle extends distally from the handpiece;
wherein the cutter is translatable within the first lumen to sever a tissue protruding through the transverse aperture and surround the inclined surface, wherein the cutter defines the second lumen;
a vacuum pump operable to draw the tissue proximally through the second lumen;
a tube axially aligned with the second lumen, wherein the tube defines a third lumen;
a pressure pump operable to push a marker out the third lumen, through the second lumen, against the inclined surface and out the transverse aperture; and
wherein the marker is axially aligned with the second lumen while the tissue is severed, while the tissue is drawn proximally through the second lumen, and while the marker is pushed out the third lumen.

6. The apparatus of claim 5 wherein the tube is axially aligned with the second lumen while the tissue is severed; and wherein the tube is axially aligned and abutted with the cutter while the marker is pushed out the transverse aperture.

7. The apparatus of claim 6 wherein the biopsy apparatus is operable with one hand of a user from when the tissue is severed through when the marker is pushed out the transverse aperture.

8. The apparatus of claim 7 wherein the tube is attached to the handpiece while the tissue is severed and while the marker is pushed out the transverse aperture.

9. The apparatus of claim 8 wherein the handpiece further comprises the vacuum pump and the pressure pump.

10. The apparatus of claim 9 wherein the marker comprises a marker clip and a pledget.

11. A method of obtaining a tissue and placing a marker, the method comprising:
providing a handpiece, wherein a needle extends distally from the handpiece, wherein the needle comprises a first lumen and a transverse aperture in fluid communication with the first lumen;
causing the tissue to protrude through the transverse aperture with a vacuum pump;
translating a cutter within the first lumen, thereby severing the tissue, wherein the cutter defines a second lumen;
drawing the tissue proximally through the second lumen with the vacuum pump, providing a tube axially aligned with the second lumen, wherein the tube is removably attached to the handpiece;
pushing the marker out the tube, through the second lumen and out the transverse aperture; and
wherein the marker is axially aligned with the second lumen while the tissue is severed, while the tissue is drawn proximally through the second lumen, and while the marker is pushed out the tube.

12. The method of claim 11 wherein an inclined surface is located at a distal end of the second lumen, wherein the inclined surface terminates at the transverse aperture; and an end of the cutter translates past and surrounds the inclined surface.

13. The method of claim 12 further comprising a pressure pump and a drive rod; wherein the pressure pump is operable to push the drive rod, wherein the drive rod pushes the marker; and wherein the drive rod jams against the inclined surface.

14. The method of claim 13 wherein the handpiece further comprises the vacuum pump and the pressure pump.

15. The method of claim 11 wherein the marker is pushed with a push rod, wherein the push rod extends outside the handpiece and opposite relative to the needle.

16. The method of claim 11 wherein the tube is axially aligned with the second lumen while the tissue is severed; and wherein the tube is axially aligned and abutted with the cutter while the marker is pushed out the transverse aperture.

17. The method of claim 11 wherein the tube is attached to the handpiece while the tissue is severed and while the marker is pushed out the transverse aperture.

18. The method of claim 11 wherein the cutter and the tube have the same inner diameter.

\* \* \* \* \*

UNITED STATES PATENT AND TRADEMARK OFFICE
CERTIFICATE OF CORRECTION

Page 1 of 1

PATENT NO. : 9,993,232 B2
APPLICATION NO. : 14/710846
DATED : June 12, 2018
INVENTOR(S) : Andrew N. Ellingson and David I. Ellingson It is certified that error appears in the above-identified patent and that said Letters Patent is hereby corrected as shown below:

In the Claims

Column 11, Claim 1, Line 52, "while the the" should be --while the marker is pushed out the tube; and the marker and the tube are proximally spaced from the--.

Signed and Sealed this
Seventh Day of August, 2018

Andrei Iancu
*Director of the United States Patent and Trademark Office*